United States Patent
Takeshima

(10) Patent No.: US 11,301,961 B2
(45) Date of Patent: Apr. 12, 2022

(54) MEDICAL SIGNAL PROCESSING APPARATUS AND MODEL LEARNING APPARATUS

(71) Applicant: Canon Medical Systems Corporation, Otawara (JP)

(72) Inventor: Hidenori Takeshima, Kawasaki (JP)

(73) Assignee: Canon Medical Systems Corporation, Otawara (JP)

( * ) Notice: Subject to any disclaimer, the term of this patent is extended or adjusted under 35 U.S.C. 154(b) by 96 days.

(21) Appl. No.: 16/417,277

(22) Filed: May 20, 2019

(65) Prior Publication Data
US 2019/0362472 A1    Nov. 28, 2019

(30) Foreign Application Priority Data
May 25, 2018  (JP) .............................. JP2018-100724

(51) Int. Cl.
*G06T 5/00*  (2006.01)
*G16H 30/40*  (2018.01)
*G06N 20/00*  (2019.01)

(52) U.S. Cl.
CPC ............. *G06T 5/001* (2013.01); *G06N 20/00* (2019.01); *G06T 5/002* (2013.01); *G16H 30/40* (2018.01); *G06T 2207/10088* (2013.01); *G06T 2207/20081* (2013.01)

(58) Field of Classification Search
CPC ......... G06T 5/001; G06T 5/002; G16H 30/40; G06N 20/00
See application file for complete search history.

(56) References Cited

U.S. PATENT DOCUMENTS

| 9,594,983 | B2* | 3/2017 | Alattar | G06K 9/00671 |
|---|---|---|---|---|
| 10,496,884 | B1* | 12/2019 | Nguyen | G06N 3/0454 |
| 2013/0165788 | A1* | 6/2013 | Osumi | A61B 8/5269 |
| | | | | 600/443 |
| 2016/0113501 | A1* | 4/2016 | Hua | A61B 5/0042 |
| | | | | 600/420 |
| 2017/0258433 | A1* | 9/2017 | Gulsun | G06T 13/20 |
| 2018/0082172 | A1* | 3/2018 | Patel | G06N 3/0472 |
| 2018/0144466 | A1* | 5/2018 | Hsieh | G06T 7/0012 |
| 2019/0336033 | A1 | 11/2019 | Takeshima | |
| 2020/0274997 | A1* | 8/2020 | Elvira | H05B 47/125 |

FOREIGN PATENT DOCUMENTS

JP    2019-93126 A    6/2019

OTHER PUBLICATIONS

Google Scholar search report.*
(Continued)

*Primary Examiner* — Qun Shen
(74) *Attorney, Agent, or Firm* — Oblon, McClelland, Maier & Neustadt, L.L.P.

(57) ABSTRACT

According to one embodiment, medical signal processing apparatus includes a processing circuit. The processing circuit adjust a level of activation of a unit included in a learned model in accordance with classification of an imaging condition for a process target medical signal. The processing circuit generates an output signal by applying the learned model in which the level of activation has been adjusted, to the medical signal.

11 Claims, 14 Drawing Sheets

(56) References Cited

OTHER PUBLICATIONS

Jo Schlemper, et al., "A Deep Cascade of Convolutional Neural Networks for MR Image Reconstruction", arXiv:1703.00555[cs.CV]. https://arxiv.org/abs/1703.00555, 12 pages.
Bo Zhu, et al., "Deep learning MR reconstruction with Automated Transform by Manifold Approximation (AUTOMAP) in real-world acquisitions with imperfect training: simulation and in-vivo experiments", ISMRM Workshop on Machine Learning, Poster 46, Mar. 2018, 1 page.
Bo Zhu, et al., "Image reconstruction by domain-transform manifold learning", Nature, vol. 555, Mar. 22, 2018, 6 pages.
Japanese Office Action dated Feb. 8, 2022, issued in Japanese Patent Application No. 2018-100724.
Vanya V. Valindria. Nick Pawlowski. Martin Rajchl. Ioannis Lavdas, Eric O. Aboagye. Andrea G. Rockall, Daniel Rueckert. Ben Glocker. "Multi-Modal Learning from Unpaired Images: Application to Multi-Organ Segmentation in CT and MRI." 2018 IEEE Winter Conference on Applications of Computer Vision.

\* cited by examiner

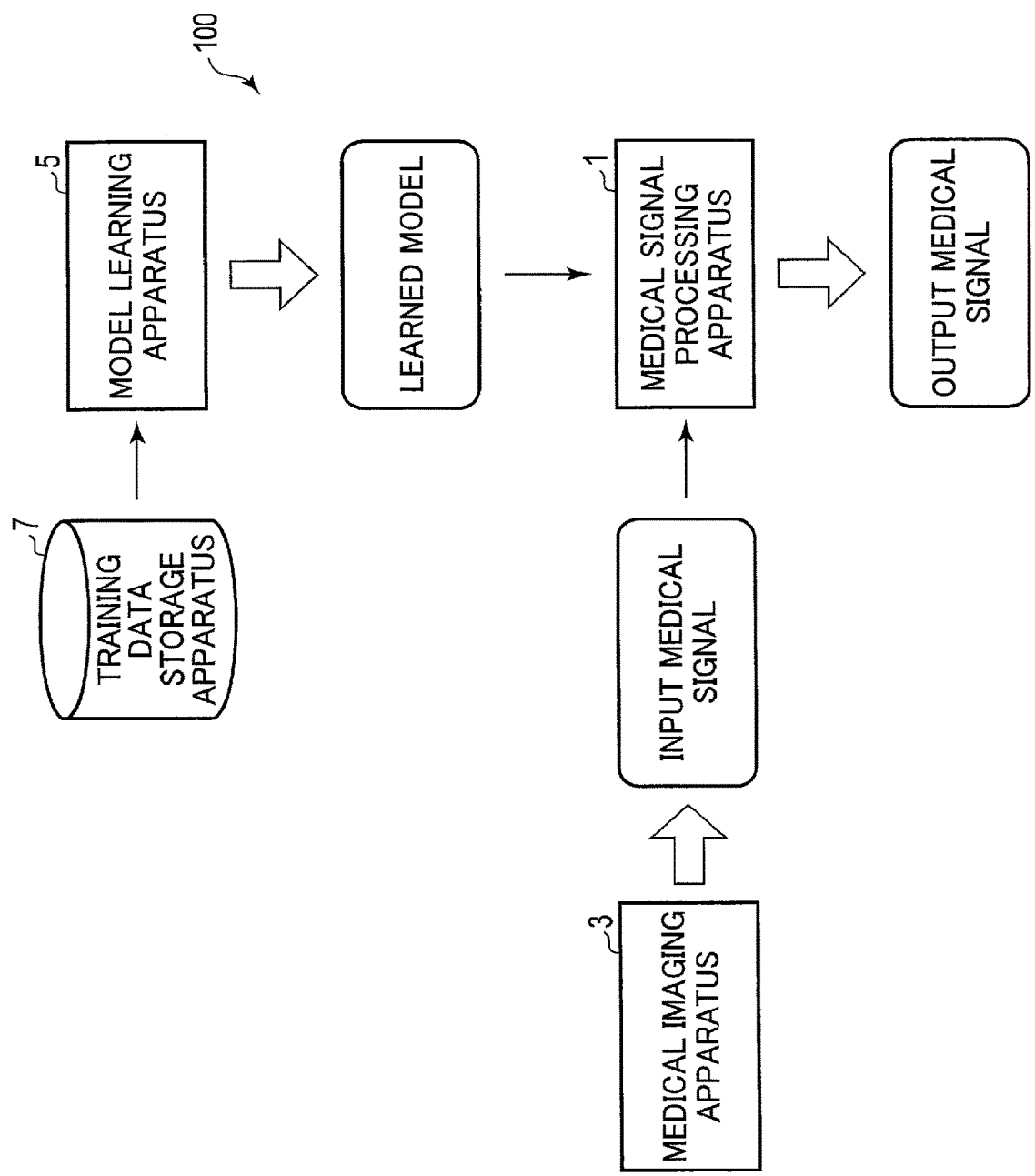
F I G. 1

| PULSE SEQUENCE | FIRST CHANNEL (INDIVIDUAL CHANNEL) | SECOND CHANNEL (INDIVIDUAL CHANNEL) | THIRD CHANNEL (INDIVIDUAL CHANNEL) | FOURTH CHANNEL (COMMON CHANNEL) |
|---|---|---|---|---|
| EPI | ON | OFF | OFF | ON |
| FSE | OFF | ON | OFF | ON |
| FE | OFF | OFF | ON | ON |
| ⋮ | ⋮ | ⋮ | ⋮ | ⋮ |

F I G. 5

CLASS: PE DIRECTION = VERTICAL
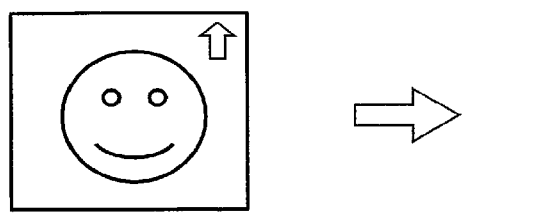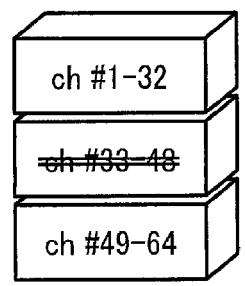
CLASS: PE DIRECTION = HORIZONTAL
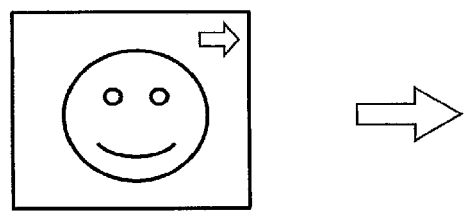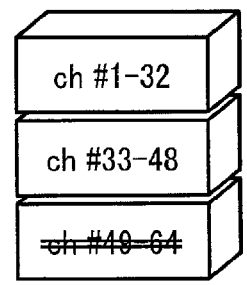
CHANNELS #33 TO 48 SERVE AS VERTICAL NOISE DENOISER
CHANNELS #49 TO 64 SERVE AS HORIZONTAL NOISE DENOISER
F I G. 12

MULTI-CLASS APPLICABLE VARIATION

CLASS: NON-EPI + CARTESIAN

CLASS: NON-EPI + RADIAL

CLASS: EPI

CLASS-DEPENDENT DENOISER SELECTION VARIATION
(COMBINATION OF ACTIVE + INACTIVE)
CLASS : EPI NOISE = 1
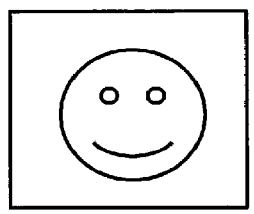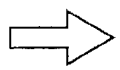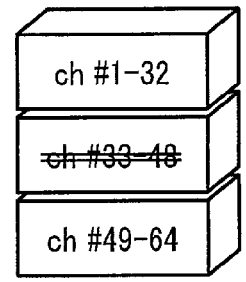
CLASS : EPI NOISE = 0
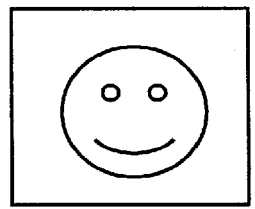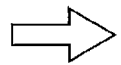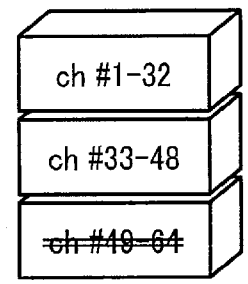
F I G. 14
| PULSE SEQUENCE TYPE | FIRST CHANNEL (INDIVIDUAL CHANNEL) | SECOND CHANNEL (INDIVIDUAL CHANNEL) | THIRD CHANNEL (COMMON CHANNEL) |
|---|---|---|---|
| EPI | 1 | 0 | 1 |
| GRASE | 0.5 | 0.5 | 1 |
| FSE | 0 | 1 | 1 |
| ⋮ | ⋮ | . | |
F I G. 15

MEDICAL SIGNAL PROCESSING APPARATUS AND MODEL LEARNING APPARATUS

CROSS-REFERENCE TO RELATED APPLICATIONS

This application is based upon and claims the benefit of priority from the prior Japanese Patent Application No. 2018-100724, filed May 25, 2018, the entire contents of which are incorporated herein by reference.

FIELD

Embodiments described herein relate generally to a medical signal processing apparatus and a model learning apparatus.

BACKGROUND

In the field of machine learning that employs medical signals such as medical image data and its raw data, a method that incorporates a deep neural network (DNN) trained with a large amount of training data may be adopted in order to restore original signals from the medical signals that contain a missing portion. Examples may include a method of generating k-space data in which the missing portion is restored by applying a DNN to the undersampled k-space data and acquiring a restored image based on the restored k-space data in magnetic resonance imaging (MRI). The examples may also include a method of directly acquiring a restored image by applying the DNN to the undersampled k-space data.

BRIEF DESCRIPTION OF THE DRAWING

FIG. 1 is a diagram showing the overview of the configuration and process of a medical signal processing system that involves a medical signal processing apparatus according to the present embodiment.

FIG. 5 is a diagram showing an example table stored in a memory of FIG. 3.

FIG. 12 is a diagram schematically showing an example activation control according to Example 1.

FIG. 14 is a diagram schematically showing an example activation control according to Application Example 2.

FIG. 15 is a diagram showing an example table according to Application Example 3.

DETAILED DESCRIPTION

Figure 2:
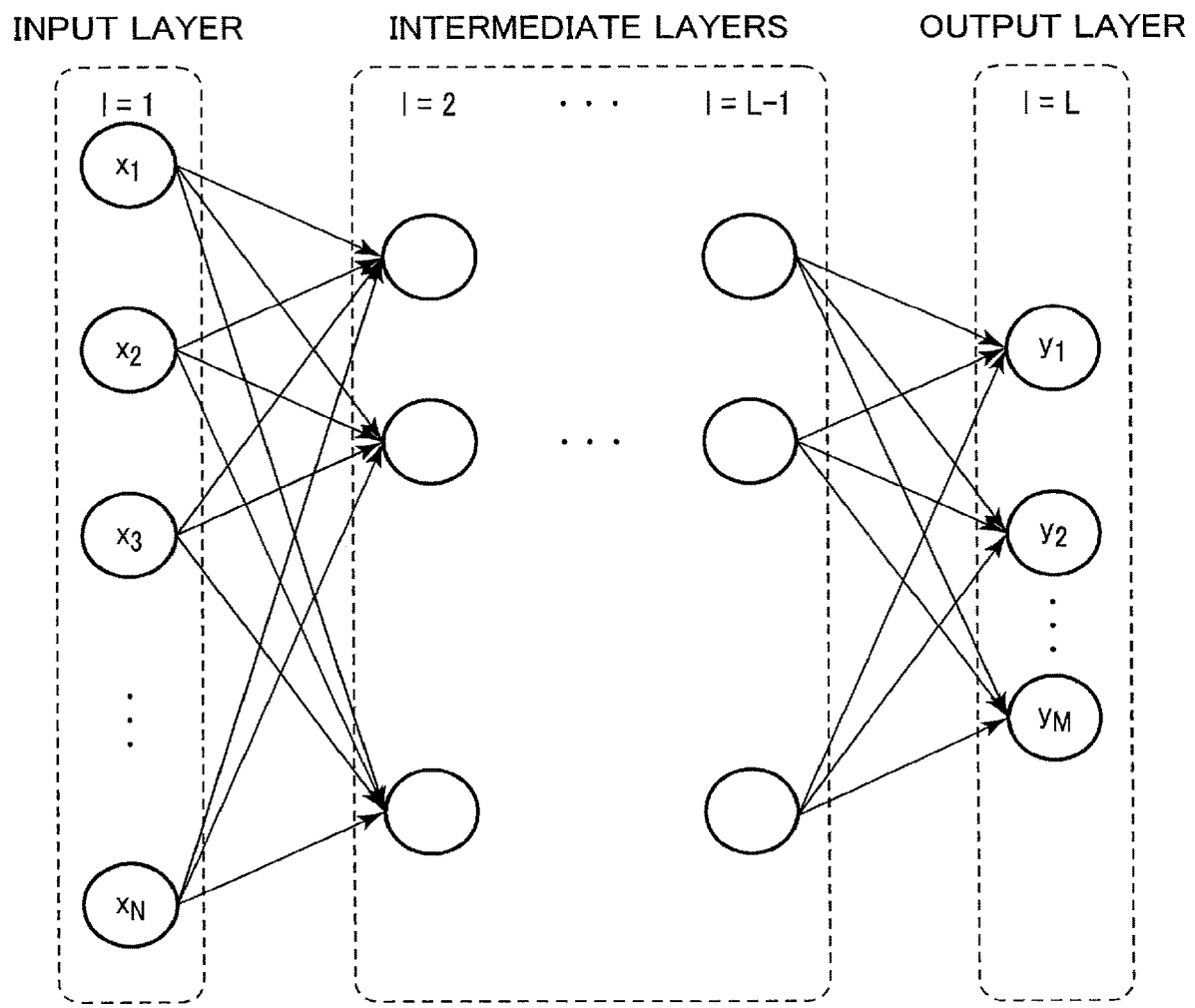
FIG. 2 is a diagram showing the overview of the configuration of a multi-layered network according to the present embodiment.

The medical signal processing apparatus according to the present embodiment is provided with a processing circuit. The processing circuit adjusts the level of activation for units included in a learned model, in accordance with the classification of imaging conditions relating to process target medical signals. The processing circuit generates an output signal by applying the learned model in which the level of activation has been adjusted, to the medical signals.

A medical signal processing apparatus and a model learning apparatus according to the present embodiment will be described below with reference to the drawings.

FIG. 1 is a diagram showing the overview of the configuration and process of a medical signal processing system 100 that involves a medical signal processing apparatus 1 according to the present embodiment. As illustrated in FIG. 1, the medical signal processing system 100 according to the present embodiment includes the medical signal processing apparatus 1, a medical imaging apparatus 3, a model learning apparatus 5 and a training data storage apparatus 7.

The training data storage apparatus 7 stores training data that includes a plurality of training samples. The training data storage apparatus 7 may be a computer provided with a mass storage device therein. The computer may be a workstation that implements image processing, a computer included in a medical image diagnostic apparatus, or an image browsing apparatus. The training data storage apparatus 7 may be a mass storage device connected to a computer in a communicable manner via a cable or a communication network. For such a storage device, a hard disk drive (HDD), a solid state drive (SSD) and an integrated circuit memory device may be adopted as appropriate.

The model learning apparatus 5 performs machine learning on machine learning models in accordance with a model learning program, based on the training data stored in the training data storage apparatus 7, and thereby generates a machine learning model that has been trained (hereinafter referred to as "learned model"). The model learning apparatus 5 is a computer, such as a workstation, having a processor such as a central processing unit (CPU) and a graphics processing unit (GPU). The model learning apparatus 5 and the training data storage apparatus 7 may be connected to each other in a communicable manner via a cable or a communication network. Alternatively, the training data storage apparatus 7 may be mounted on the model learning apparatus 5. If this is the case, the training data is supplied from the training data storage apparatus 7 to the model learning apparatus 5 via a cable, a communication network or the like.

The model learning apparatus 5 and the training data storage apparatus 7 may not be connected in a communicable manner. If this is the case, the training data is supplied from the training data storage apparatus 7 to the model learning apparatus 5 by way of a portable storage medium or the like that stores the training data.

The machine learning model according to the present embodiment is a parameter-added composite function that is obtained by combining a plurality of functions to, based on medical signals that are entered as an input, generate output signals corresponding to the medical signals. The machine learning model according to the present embodiment may be capable of outputting as an output signal a medical signal in which a signal defect portion included in an input medical signal is restored, or may be capable of outputting recognition results with regard to the input medical signal. A parameter-added composite function is defined by a combination of multiple adjustable functions and parameters. The machine learning model according to the present embodiment may be any parameter-added composite function that satisfies the above requirements as long as it is a network model having multiple layers (hereinafter referred to as a multi-layered network).

The medical imaging apparatus 3 generates a process target medical signal. Conceptually, the medical signal according to the present embodiment includes raw data acquired by the medical imaging apparatus 3 or any other medical imaging apparatus that performs medical imaging on the subject, and medical image data generated by performing restoration processing on the raw data. The medical imaging apparatus 3 may be any modality apparatus capable of generating medical signals. For example, the medical imaging apparatus 3 according to the present embodiment may be a single modality apparatus such as a magnetic resonance imaging (MRI) apparatus, an X-ray computed tomography imaging (CT) apparatus, an X-ray diagnostic apparatus, a positron emission tomography (PET) apparatus, a single photon emission CT (SPECT) apparatus or an ultrasonic diagnostic apparatus. Alternatively, it may be a complex modality apparatus such as a PET/CT apparatus, SPECT/CT apparatus, PET/MRI apparatus, or SPECT/MRI apparatus.

The raw data according to the present embodiment is not limited to the original raw data acquired by the medical imaging apparatus 3. The raw data according to the present embodiment may be computational raw data, which is generated by executing the forward projection processing on the medical image data. The raw data according to the present embodiment may be raw data obtained by executing any signal processing, such as signal compression processing, resolution decomposition processing, signal interpolation processing, and resolution synthesis processing, on the original raw data. The raw data according to the present embodiment, if it is three-dimensional raw data, may be hybrid data subjected to the restoration processing for one or two axes only. In the same manner, the medical image according to the present embodiment is not limited to an original medical image generated by the medical imaging apparatus 3. The medical image according to the present embodiment may be a medical image obtained by executing any image processing, such as image compression processing, resolution decomposition processing, image interpolation processing, and resolution synthesis processing, on the original medical image.

The medical signal processing apparatus 1 generates an output signal corresponding to the process target input medical signal acquired by the medical imaging apparatus 3, using a learned model obtained by the model learning apparatus 5 in accordance with a model learning program. The medical signal processing apparatus 1 and the model learning apparatus 5 may be connected to each other in a communicable manner via a cable or a communication network. Alternatively, the medical signal processing apparatus 1 and the model learning apparatus 5 may be mounted on the same computer. If this is the case, a learned model is supplied from the model learning apparatus 5 to the medical signal processing apparatus 1 via a cable, a communication network or the like. The medical signal processing apparatus 1 and the model learning apparatus 5 may not always be connected to each other in a communicable manner. If this is the case, the learned model is supplied from the model learning apparatus 5 to the medical signal processing apparatus 1 by way of a portable storage medium or the like that stores the learned model. The learned model may be supplied at any time, i.e., at any time point between the manufacture of the medical signal processing apparatus 1 and installing of the medical signal processing apparatus 1 in a medical facility or the like, or at the time of maintenance. The supplied learned model is stored in the medical signal processing apparatus 1. The medical signal processing apparatus 1 may be a computer mounted on a medical image diagnostic apparatus having a medical imaging apparatus 3 thereon, or a computer connected to such a medical image diagnostic apparatus via a cable or network in a communicable manner. Alternatively, it may be a computer provided independently from the medical image diagnostic apparatus.

The overview of the configuration of a multi-layered network according to the present embodiment is explained below. The multi-layered network here means a network having an architecture in which only adjacent layers in a laminated arrangement are coupled to each other so that information propagates in one direction from the input layer side to the output layer side. As illustrated in FIG. 2, the multi-layered network according to the present embodiment is constituted by L layers, namely, an input layer (l=1), intermediate layers (l=2, 3, . . . , L−1), and an output layer (l=L). An example of the multilayer network is described below, although its configuration is not limited to this description.

When the l-th layer includes the number I of units, Equation (1-1) represents the input $u^{(l)}$ to the l-th layer, and Equation (1-2) represents the output $z^{(l)}$ from the l-th layer. Then, the relationship between the input to the l-th layer and the output from the l-th layer can be expressed by Equation (1-3).

[Expression 1]

$$u^{(l)} = (u_1, u_2, u_3, \ldots, u_I) \tag{1-1}$$

$$z^{(l)} = (z_1, z_2, z_3, \ldots, z_I) \tag{1-2}$$

$$z^{(l)} = f(u^{(l)}) \tag{1-3}$$

The superscript (l) indicates the layer number. Furthermore, f(u) in Equation (1-3) is an activation function, for which any function can be selected in accordance with the purpose from various functions such as a logistic sigmoid function (logistic function), hyperbolic tangent function, rectified liner unit (ReLU), linear mapping, identity mapping, and max-out function.

When the (l+1)-th layer includes the number J of units, Equation (2-1) represents the weighting matrix $W^{(l+1)}$ between the l-th layer and the (l+1)-th layer, and Equation (2-2) represents the bias $b^{(l+1)}$ in the (l+1)-th layer. The input $u^{(l+1)}$ to the (l+1)-th layer and the output $z^{(l+1)}$ from the (l+1)-th layer therefore can be represented by Equations (2-3) and (2-4), respectively.

[Expression 2]

$$W^{(l+1)} = \begin{pmatrix} w_{11} & \cdots & w_{1I} \\ \vdots & \ddots & \vdots \\ w_{J1} & \cdots & w_{JI} \end{pmatrix} \quad (2\text{-}1)$$

$$b^{(l+1)} = (b_1, b_2, b_3, \ldots, b_J) \quad (2\text{-}2)$$

$$u^{(l+1)} = W^{(l+1)}z^{(l)} + b^{(l+1)} \quad (2\text{-}3)$$

$$z^{(l+1)} = f(u^{(l+1)}) \quad (2\text{-}4)$$

In the multi-layered network according to the present embodiment, the medical signal expressed by Equation (3-1) is input to the input layer (l=1). In this input layer, since the input data x directly becomes the output data $z^{(l)}$, the relationship expressed by Equation (3-2) is established.

[Expression 3]

$$x = (x_1, x_2, x_3, \ldots, x_N) \quad (3\text{-}1)$$

$$z^{(1)} = x \quad (3\text{-}2)$$

Any medical signal that is to be input to the input layer will be referred to as "input medical signal". For the input medical signal x, various forms are adoptable in accordance with the purpose. Several typical examples are listed below.

(1) Form that defines each of its components $x_p$ (p=1, 2, . . . , N) as a value (pixel value or voxel value) of the position in an image data item, where one image data item is adopted for the input medical signal x.

(2) Form that assigns the area of an input unit to each image data item in the input layer, where M items of image data (e.g., multiple items of image data with different imaging conditions) are adopted for the input medical signal x, determining a component $x_p$ where 1≤p≤q is the first image data item, a component $x_p$ where q+1≤p≤r is the second image data item, a component $x_p$ where r+1≤p≤s is the third image data, and so on.

(3) Form that defines a component $x_p$ as a vector in which values of positions (pixel values or voxel values) in a single image data item are vertically provided, where M items of image data are adopted for the input medical signal x.

(4) Form that adopts any of (1) to (3), where the raw data such as k-space data and projection data is adopted for the input medical signal x.

(5) Form that adopts any of (1) to (3), where image data or raw data that has been subjected to a convolutional process is adopted for the input medical signal x.

For the intermediate layers (l=2, 3, . . . , L−1) subsequent to the input layer, outputs $z^{(2)}, \ldots z^{(L-1)}$ of the layers can be calculated by sequentially executing the calculations of Equations (2-3) and (2-4).

The output $z^{(L)}$ of the output layer (L-th layer) is expressed by Equation (4-1) below. The multilayer network according to the present embodiment is a forward propagation network in which the image data x that is input to the input layer propagates from the input layer side to the output layer side with only adjacent layers being coupled to each other. Such a forward propagation network can be expressed as a composite function as in Equation (4-2).

[Expression 4]

$$z^{(L)}: y = z^{(L)} \quad (4\text{-}1)$$

$$\begin{aligned} y(x) &= f(u^{(L)}) \quad (4\text{-}2) \\ &= f(W^{(L)}z^{(L-1)} + b^{(L)}) \\ &= f(W^{(L)}f(W^{(L-1)}z^{(L-2)} + b^{(L-1)}) + b^{(L)}) \\ &= f(W^{(L)}f(W^{(L-1)}f(\ldots f(W^{(l)}z^{(l-1)} + b^{(l)} \ldots)) + b^{(L)}) \end{aligned}$$

The composite function of Equation (4-2) is defined as a combination of a linear correlation between the layers using the weighting matrix $W^{(l+1)}$, a nonlinear correlation (or linear correlation) using an activation function $f(u^{(l+1)})$ of the layers, and bias $b^{(l+1)}$, based on Equations (2-3) and (2-4). In particular, the weighting matrix $W^{(l+1)}$ and bias $b^{(l+1)}$ are referred to as network parameters p of the network. The composite function defined by Equation (4-2) changes the form of a function, depending on the selected parameter p. For this reason, by selecting a suitable parameter p of Equation (4-2), the multi-layered network according to the present embodiment can be defined as a function that allows the output layer to output a desired result y.

The medical signal processing system 100 using a multi-layered network according to the present embodiment will be described in detail below. In the following description, the medical signal processing apparatus 1 is coupled to the medical imaging apparatus 3, and incorporated, together with the medical imaging apparatus 3, into a medical image diagnostic apparatus.

Figure 3:
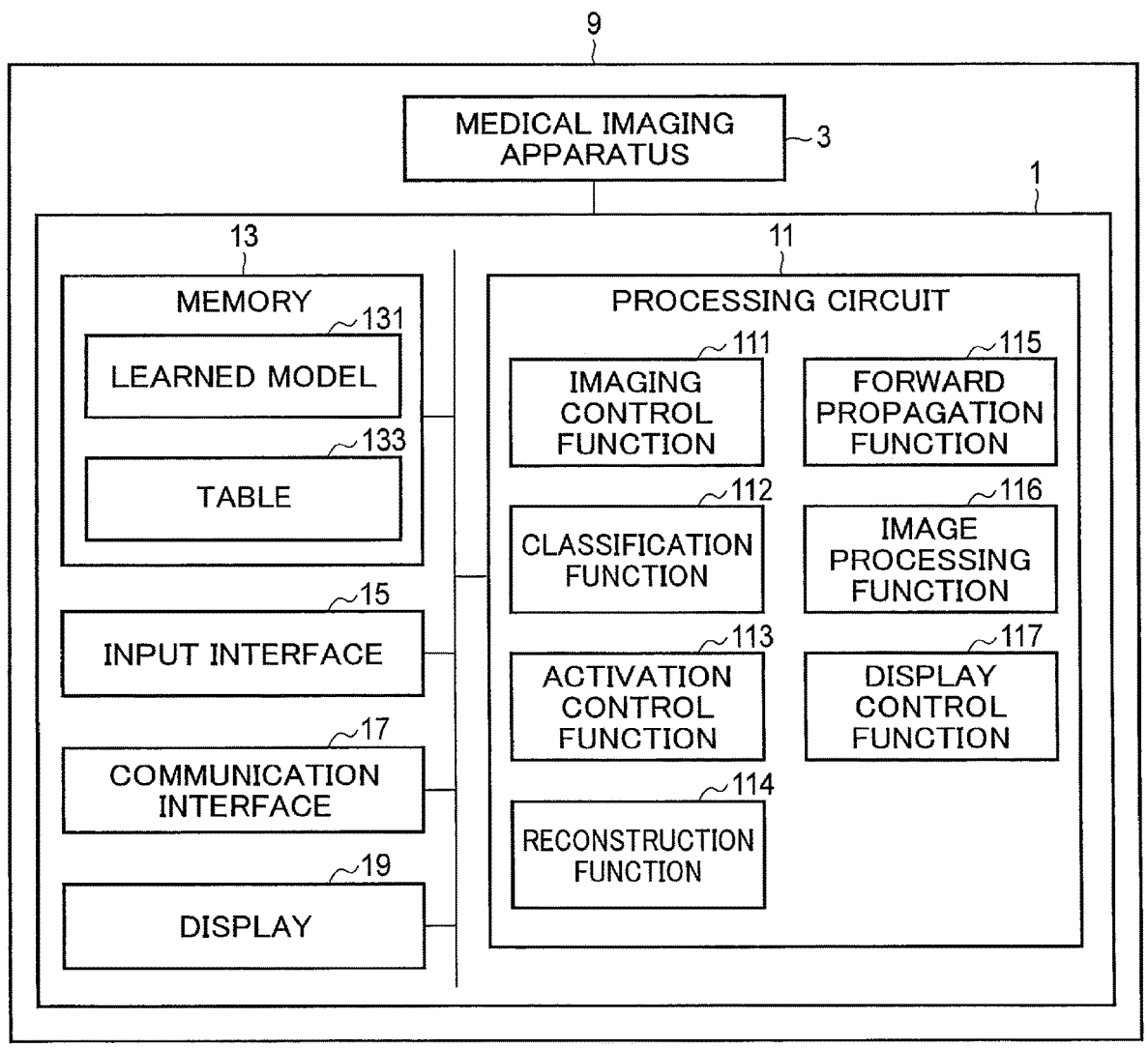
FIG. 3 is a diagram showing the configuration of a medical image diagnostic apparatus according to the present embodiment.

FIG. 3 is a diagram showing the configuration of a medical image diagnostic apparatus 9 according to the present embodiment. As illustrated in FIG. 3, the medical image diagnostic apparatus 9 includes a medical signal processing apparatus 1 and a medical imaging apparatus 3. In one example, the medical imaging apparatus 3 may correspond to a gantry, and the medical signal processing apparatus 1 may correspond to a console connected to the gantry. The medical signal processing apparatus 1, however, may be arranged in the gantry of the medical image diagnostic apparatus 9, or may be realized by a component that is different from the console or gantry of the medical image diagnostic apparatus 9. If the medical image diagnostic apparatus 9 is a magnetic resonance imaging apparatus, the different component may be a computer or a dedicated computing machine other than the console, which may be installed in a machine room.

The medical imaging apparatus 3 performs medical imaging for the subject in accordance with the imaging principles corresponding to the modality type of the medical imaging apparatus 3, and acquires raw data of the subject. The acquired raw data is transferred to the medical signal processing apparatus 1. For example, the raw data may be k-space data for the medical imaging apparatus 3 being a magnetic resonance imaging apparatus, and projection data or sinogram data for an X-ray computed tomography imaging apparatus. The raw data may be echo data for an ultrasonic diagnostic apparatus, coincidence data or sinogram data for a PET apparatus, and projection data or sinogram data for a SPECT apparatus.

When the medical imaging apparatus 3 is the gantry of the magnetic resonance imaging apparatus, this gantry repeatedly applies gradient magnetic field by way of a gradient magnetic field coil and RF pulse by way of a transmission coil, with a static magnetic field applied by way of a static magnetic field magnet. An MR signal is released from the subject in response to the application of the RF pulse. The emitted MR signal is received via the reception coil. The received MR signal is subjected to the signal processing such as A/D conversion by the reception circuit. The A/D converted MR signal is referred to as k-space data. The k-space data is transferred as raw data to the medical signal processing apparatus 1.

If the medical imaging apparatus 3 is the gantry of the X-ray computed tomography imaging apparatus, the gantry applies X-rays from the X-ray tube to the subject, while rotating the X-ray tube and the X-ray detector around the subject, and detects by an X-ray detector the X-rays that have passed through the subject. In the X-ray detector, an electric signal having a wave-height value corresponding to the detected X-ray dose is generated. This electric signal is subjected to signal processing such as A/D conversion by a data acquisition circuit. The A/D converted electrical signal is referred to as projection data or sinogram data. The projection data or sinogram data is transferred as raw data to the medical signal processing apparatus 1.

As illustrated in FIG. 3, the medical signal processing apparatus 1 includes, as hardware resources, a processing circuit 11, a memory 13, an input interface 15, a communication interface 17, and a display 19.

The processing circuit 11 includes a processor such as a CPU and GPU. When activating the program installed in the memory 13 or the like, the processor implements an imaging control function 111, classification function 112, activation control function 113, reconstruction calculation function 114, forward propagation function 115, image processing function 116, and display control function 117. Each of the functions 111 to 117 does not have to be realized by a single processing circuit. A plurality of independent processors may be combined into a processing circuit, and each of the processors may execute the program to realize the functions 111 to 117.

With the imaging control function 111, the processing circuit 11 controls the medical imaging apparatus 3 in accordance with imaging conditions to perform medical imaging on the subject. The imaging conditions according to the present embodiment include imaging principles of the medical imaging apparatus 3 and various imaging parameters. The imaging principles correspond to the type of the medical imaging apparatus 3, or more specifically, to a magnetic resonance imaging apparatus, X-ray computed tomography imaging apparatus, PET apparatus, SPECT apparatus or ultrasonic diagnostic apparatus. The imaging parameters may include the field of view (FOV), imaging body part, slice position, frame (time phase of a medical image), matrix size, and presence or absence of a contrast agent. In addition to the above, the imaging parameters for magnetic resonance imaging may further include the type of pulse sequences, parameters such as repetition time (TR), echo time (TE), flip angle (FA), and type of k-space trajectory. The imaging parameters for X-ray computer tomography may further include X-ray conditions (tube current, tube voltage, X-ray exposure duration, etc.), the type of scanning (spectral CT, integral CT, non-helical scanning, helical scanning, gated scanning, etc.), tilt angle, rotation speed, spatial resolution of the detector, and the like. Other imaging conditions according to the present embodiment may include a data defect portion in a medical signal of raw data or medical image data.

With the classification function 112, the processing circuit 11 classifies medical signals in accordance with the type of imaging condition relating to the process target medical signal such as the raw data or medical image data. Hereinafter, the classification corresponding to the type of imaging condition will be referred to as a class, and the identifier of the classification corresponding to the type of imaging condition will be referred to as a class value. The class value may be the name of the type of imaging condition, or may be any letter or symbol.

With the activation control function 113, the processing circuit 11 adjusts the level of activation of units included in a learned model 131, or in other words the degree of association between units of different layers, in accordance with the class of the imaging condition for the process target medical signal such as raw data or medical image data. According to the present embodiment, the parameter that represents the level of activation of a unit, or in other words the parameter that represents the degree of association between units of different layers, will be referred to as a layer-switching parameter. The processing circuit 11 adjusts the value of the layer-switching parameter for each unit, using a table 133 stored in the memory 13. The table 133 may be created by the model learning apparatus 5. The table 133 will be discussed later. According to the present embodiment, the weighting matrix W and bias b are collectively referred to simply as parameters, which should be differentiated from layer-switching parameters.

With the reconstruction calculation function 114, the processing circuit 11 performs image reconstruction processing on the raw data transmitted from the medical imaging apparatus 3 to reconstruct a medical image. The image reconstruction according to the present embodiment may be divided into analytical image reconstruction and iterative image reconstruction. As the analytical image reconstruction for MR image reconstruction, Fourier transform or inverse Fourier transform may be adopted. As the analytical image reconstruction for CT image reconstruction, filtered back projection (FBP), convolution back projection (CBP), or application of these projections may be adopted. As iterative image reconstruction, expectation maximization (EM), algebraic reconstruction technique (ART), or application of these techniques may be adopted. The processing circuit 11 may perform an inverse transform with respect to the image reconstruction on the medical image, thereby generating raw data. For example, when the image reconstruction is carried out by Fourier transform, its inverse transform is inverse Fourier transform. When the image reconstruction is carried out by inverse Radon transform, its inverse transform is Radon transform.

With the forward propagation function 115, the processing circuit 11 applies the learned model 131 having its activation level (layer-switching parameter) adjusted in accordance with the activation control function 113, to the process target medical signal such as the raw data or medical image data, thereby generating an output signal. The type of output signal depends on the type of learned model 131. For example, if the learned model 131 is a machine learning model for image recognition, the recognition results are output as an output signal. If the learned model 131 is a machine learning model for restoring a signal missing portion, a medical signal having the signal defect portion restored is output as an output signal. The learned model 131 will be described later.

With the image processing function 116, the processing circuit 11 performs various types of image processing on the medical images generated by the reconstruction calculation function 114, the output signals generated by the forward propagation function 115, and the like. For example, the processing circuit 11 may perform three-dimensional image processing such as volume rendering, surface rendering, pixel value projection processing, multi-planer reconstruction (MPR) processing, and curved MPR (CPR) processing.

With the display control function 117, the processing circuit 11 displays various information on the display 19. For example, the processing circuit 11 may display medical images generated by the reconstruction calculation function 114, output signals generated by the forward propagation function 115, and medical images processed by the image processing function 116. The processing circuit 11 may also display class values of medical signals determined by the classification function 112, the table 133, and the like.

The memory 13 is a storage device that stores various information, such as a read only memory (ROM), random access memory (RAM), hard disk drive (HDD), solid state drive (SSD), and integrated circuit memory device. The memory 13 may store the learned model 131 generated by the model learning apparatus 5 and the table 133. Instead of the above mentioned storage devices, the memory 13 may be a portable storage medium such as a compact disc (CD), a digital versatile disc (DVD), and a flash memory, or a drive device that reads and writes various types of information from and to a semiconductor memory element. The memory 13 may be provided in a computer coupled to the medical signal processing apparatus 1 via a network.

The input interface 15 receives various input operations from the user, converts the received input operations into electric signals, and outputs the signals to the processing circuit 11. Specifically, the input interface 15 is coupled to input devices such as a mouse, a keyboard, a track ball, a switch, a button, a joystick, a touch pad and a touch panel display. The input interface 15 outputs to the processing circuit 11 an electric signal corresponding to the input operation to the input device. In addition, the input device coupled to the input interface 15 may be an input device provided in a computer coupled via a network or the like.

The communication interface 17 is an interface for performing data communications with the medical imaging apparatus 3, the model learning apparatus 5, and the training data storage apparatus 7, as well as other computers.

The display 19 displays various types of information in accordance with the display control function 117 of the processing circuit 11. The display 19 may display medical images generated by the reconstruction calculation function 114, output signals generated by the forward propagation function 115, and medical images subjected to image processing by the image processing function 116. The display 19 outputs a graphical user interface (GUI) or the like for receiving various operations from the user. As the display 19, a liquid crystal display (LCD), a cathode ray tube (CRT) display, an organic electroluminescence display (OELD), a plasma display, or any other display may be suitably employed.

Figure 4:
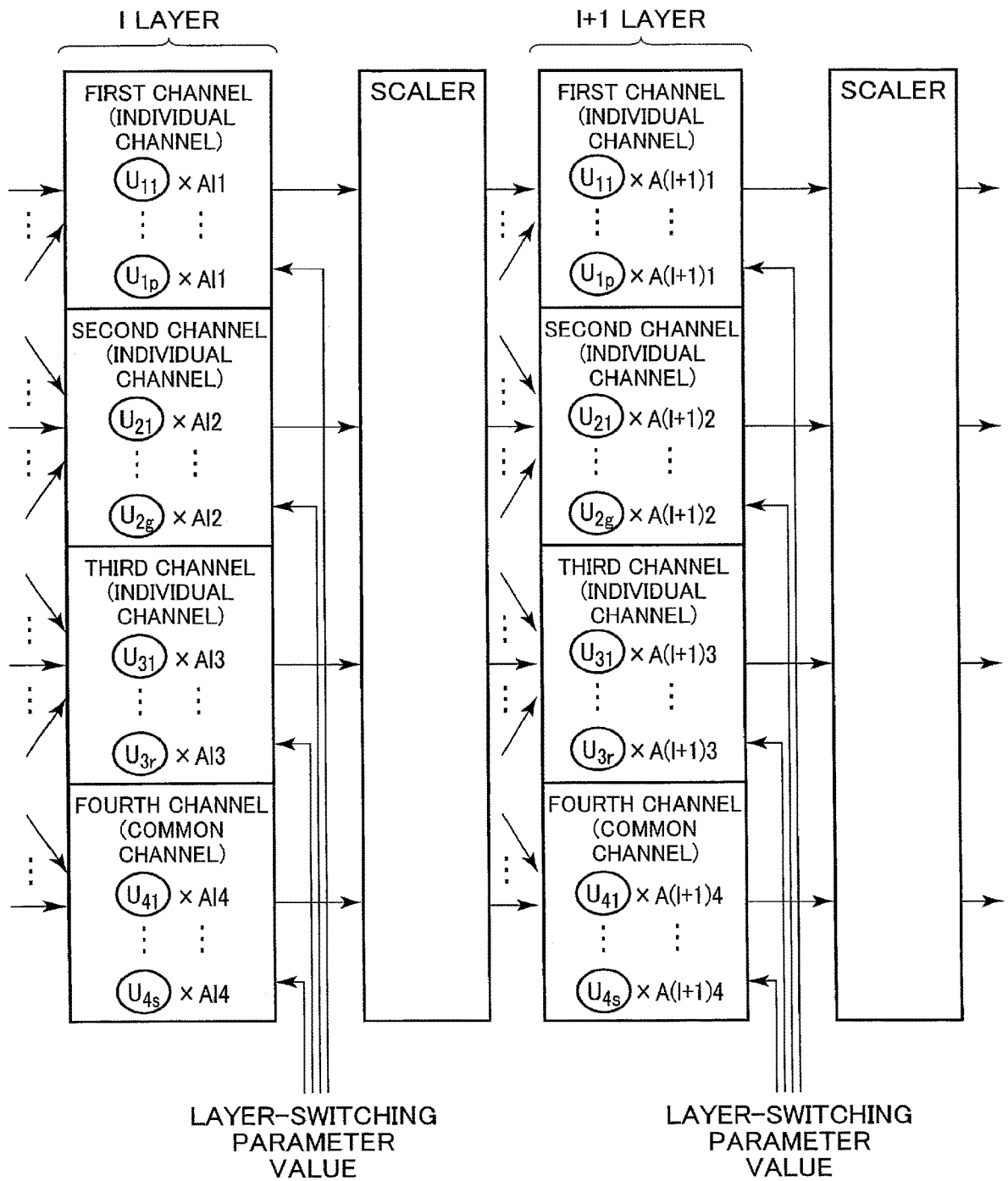
FIG. 4 is a diagram showing the configuration of intermediate layers in the multi-layered network according to the present embodiment.

Next, the configuration of intermediate layers in the multi-layered network according to the present embodiment will be explained. FIG. 4 shows the configuration of the intermediate layers in the multi-layered network according to the present embodiment.

As illustrated in FIG. 4, each layer 1 of the intermediate layers includes a plurality of units $U_{ab}$. The units according to the present embodiment are classified into groups, the number of which is smaller than the number of units in each layer. Hereinafter, a group of units will be referred to as a channel. The first digit of the suffix of "U" denotes the number of the channel to which the unit belongs, and the second digit denotes the number of the unit in this channel. For simplicity, FIG. 4 illustrates only one output from each channel. In actuality, each unit of each channel produces an output. In addition, for simplicity, FIG. 4 illustrates only one input to each channel. In actuality, each unit of each channel receives an input.

For the multi-layered network according to the present embodiment, parameters are trained using medical signals relating to the imaging conditions of various classes so that the multi-layered network becomes applicable to medical signals relating to the imaging conditions of various classes. The units in the multi-layered network according to the present embodiment can be classified into a common channel, which is a group of units that relates to all the classes used for training, and an individual channel, which is a group of units that is limited to a single class or some of the classes that are fewer than the number of all the classes. For instance, the units included in the layers 1 in FIG. 4 are classified into four channels, where the first channel, second channel and third channel are assigned to individual channels, and the fourth channel is assigned to a common channel. For simplicity, the channels of FIG. 4 are classified in order of unit number. The units of the same channel, however, may be distributed in each layer.

The common channel significantly contributes to the output signals for the input medical signals of all the classes. An individual channel significantly contributes to the output signal only when an input medical signal of a related class is input, and does not significantly contribute to the output signal if an input medical signal of an unrelated class is input.

A layer-switching parameter $A_{ab}$ is attached to a unit according to the present embodiment. The first digit of the suffix of the layer-switching parameter $A_{ab}$ denotes the number of the layer to which the unit belongs, and the second digit denotes the number of the channel in this layer.

For instance, the layer-switching parameter $A_{ab}$ may be in binary form, including the ON value indicating that the unit is ON (activated state) and the OFF value indicating that the unit is OFF (non-activated state). The layer-switching parameter of any unit that belongs to the common channel is always set to the ON value. As for the units that belong to an individual channel, their layer-switching parameters are set to the ON value when the input medical signal is of the class that relates to this individual channel, while the layer-switching parameters are set to the OFF value when the input medical signal is of the class that does not relate to the individual channel. When the layer-switching parameter is set to the ON value, or in other words, when the unit is ON, the network to which the unit belongs will be connected so that output data z is output from this unit. When the layer-switching parameter is set to the OFF value, or in other words, when the unit is OFF, the network to which the unit belongs will be cut off so that no output data z is output from the unit. Hereinafter, the layer-switching parameter being set to the ON value may be referred to as activation, and the layer-switching parameter being set to the OFF value may be referred to as non-activation. The ON value represents a higher level of activation than the OFF value.

The layer-switching parameter $A_{ab}$ is a variable that differs from the weighting matrix W or bias b. For instance, as illustrated in FIG. 4, the layer-switching parameter $A_{ab}$ is multiplied by the output of the corresponding unit. The same value is given to the layer-switching parameters $A_{ab}$ of the same channel in the same layer. In this manner, the layer-switching parameters can be set for each channel in accordance with the class.

With the activation control function 113, the processing circuit 11 switches the layer-switching parameter of the individual channel between the ON value and the OFF value in accordance with the class of the input medical signal. In this manner, the multi-layered network can be optimized for the class of the input medical signals. That is, the multi-layered network according to the present embodiment incorporates a common channel that is a class-independent network and an individual channel that is a class-dependent network. Thus, in comparison with all the layer-switching parameters being set to the ON value regardless of the class of the input medical signal, the speed and accuracy of the calculation can be improved. Furthermore, by providing a common channel and individual channels, the common channel can carry out the calculation common to all the classes, while the individual channels can carry out a calculation common to the corresponding classes. If a learned model needs to be generated by individual channels only, channels that correspond to the common channel and overlap for the number of to-be-processed classes will be required for the learned model. In contrast, the learned model according to the present embodiment, which is provided with a common channel and individual channels, can reduce the number of units.

As illustrated in FIG. 4, a scaler is provided between the layers. The scaler compensates for the number of units that are suspended by the layer-switching parameter. Specifically, a scaler is coupled for every connection of an immediately previous unit with the subsequent unit. Each scaler receives the output data from the previous unit, multiplies the compensation parameter for the received output data, and outputs the resultant data to the subsequent unit. The compensation parameter is set to the value obtained by dividing the total number of previous units by the number of ON-state units. For example, when the total number of previous units is 64, of which 16 units are in the OFF state, the scaler multiplies the output values of the previous units by 64/48. The compensation parameters of the scalers that belong to the same layer are set to the same value. The compensation parameters may be determined by the processing circuit 11 with the activation control function 113.

With the activation control function 113, the processing circuit 11 adjusts the layer-switching parameter for each unit, using the table 133 stored in the memory 13. The table 133 is a look-up table (LUT) that stores the relationship between units and layer-switching parameters for each class. The processing circuit 11 identifies the layer-switching parameter for each unit to which the class relating to the process target medical signal belongs, using the table 133, and adjusts the layer-switching parameter of each unit of the learned model 131 to the identified layer-switching parameter of the unit. The same layer-switching parameter may be assigned to the units of the same channel, or the layer-switching parameters may be assigned in accordance with a separately defined rule (e.g., rule of alternating the layer-switching parameter between "ON" and "OFF").

FIG. 5 shows an example table 133. As illustrated in FIG. 5, the types of pulse sequences are adopted as classes for the table 133 of FIG. 5, and units are denoted as channels. The types of pulse sequences may include echo planar imaging (EPI), fast spin echo (FSE), and field echo (FE). It is assumed that four channels are present in the same manner as in FIG. 4. The first channel, second channel, and third channel are individual channels, whereas the fourth channel is a common channel.

With the activation control function 113, the processing circuit 11 searches the table 133 stored in the memory 13, using as a search key the class value determined by the classification function 112 to identify the layer-switching parameter for each unit relating to this class value, and adjusts the layer-switching parameter of each unit of the learned model 131 to the identified layer-switching parameter. In this manner, the connection of the units of the learned model can be dynamically optimized in accordance with the class of the input medical signal.

As illustrated in FIG. 5, if the type of pulse sequence is EPI, the layer-switching parameter of the first channel is adjusted to "ON", the layer-switching parameter of the second channel is adjusted to "OFF", the layer-switching parameter of the third channel is adjusted to "OFF", and the layer-switching parameter of the fourth channel is adjusted to "ON". If the type of pulse sequence is FSE, the layer-switching parameter of the first channel is adjusted to "OFF", the layer-switching parameter of the second channel is adjusted to "ON", the layer-switching parameter of the third channel is adjusted to "OFF", and the layer-switching parameter of the fourth channel is adjusted to "ON". If the type of pulse sequence is FE, the layer-switching parameter of the first channel is adjusted to "OFF", the layer-switching parameter of the second channel is adjusted to "OFF", the layer-switching parameter of the third channel is adjusted to "ON", and the layer-switching parameter of the fourth channel is adjusted to "ON".

The input medical signals do not have to be classified for all the elements of the imaging conditions, as long as the input medical signals are classified for the classes targeted for the reconstruction of the learned model 131. For instance, if a learned model 131 that can realize the reconstruction in accordance with the above three types of pulse sequences is to be generated, the input medical signal suffices as long as it is classified into one of the three types of pulse sequences. Thus, the elements of imaging conditions other than the above three types of pulse sequences such as a k-space trajectory scheme and imaging body part do not always have to be classified. Similarly, the table 133 may simply store the relationship between the layer-switching parameters and units only for the classes that are to be reconstructed by the learned model 131.

Next, the example operations of the medical signal processing apparatus 1 according to the present embodiment will be explained. In the following explanation, the learned model is a multi-layered network that restores a signal defect. As a multi-layered network, a deep neural network (DNN) designed to resemble the neural circuit of the brain of a living being is adopted. According to the present embodiment, a signal defect is a concept that includes any difference between a desired medical signal of a subject and the actual medical signal. For example, signal defects may include signal degradation due to noise produced by various causes, signal missing due to a reduced number of sampling positions of the medical signals by sparse sampling of the projection data and k-space data, and information missing due to the conversion of continuous values to discrete values that may occur during the A/D conversion.

The processing circuit 11 according to the present embodiment uses the learned model 131 to carry out DNN reconstruction, by which medical image data having the signal defect portion restored can be reconstructed from signal-defect containing raw data. As raw data to which the learned model 131 is applied, various types of raw data generated by the medical imaging apparatus 3 may be adopted. In the following explanation of the DNN reconstruction, it is assumed that the raw data is k-space data acquired by the magnetic resonance imaging apparatus.

Figure 6:
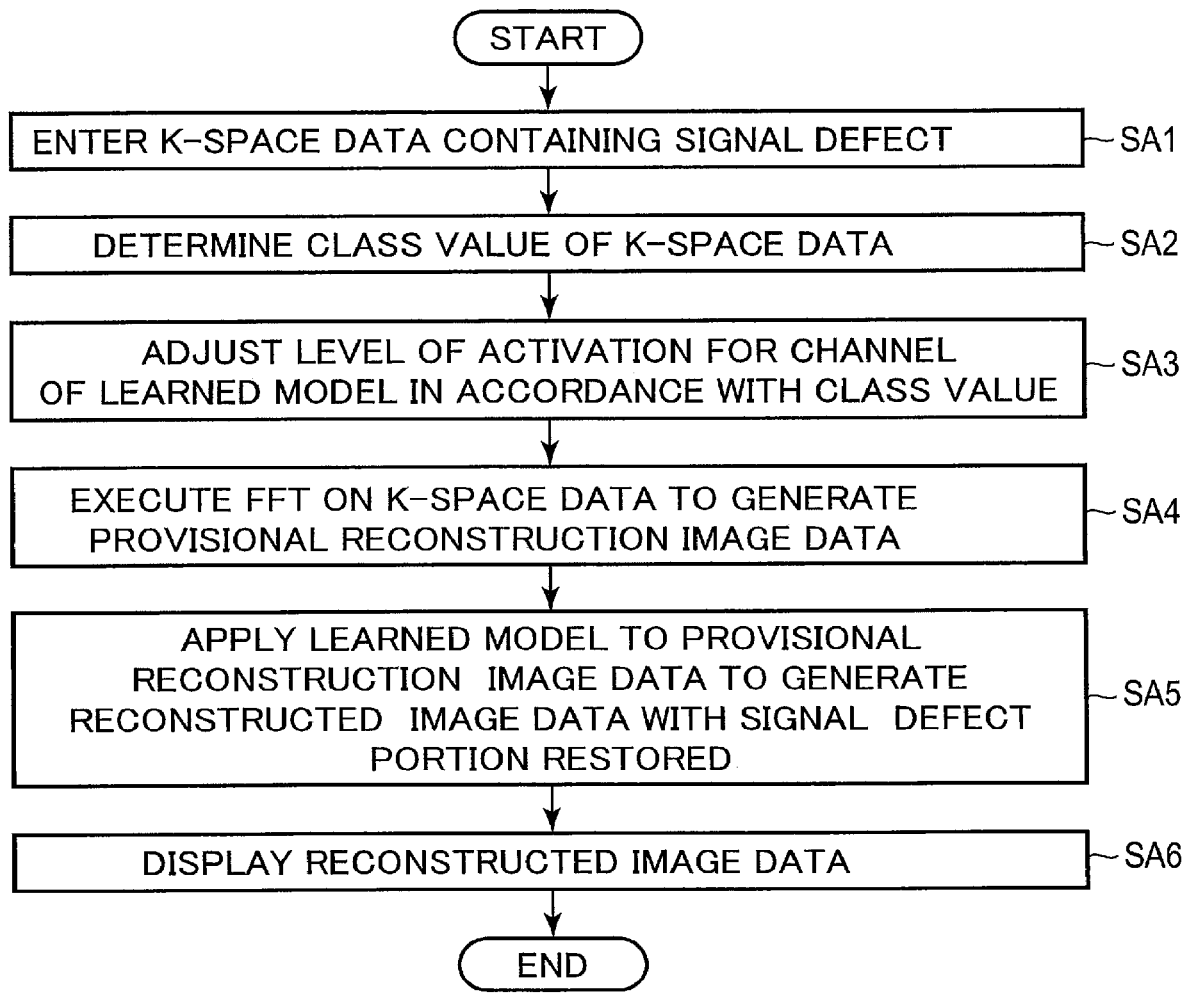
FIG. 6 is a diagram showing the flow of the DNN reconstruction processing implemented by a processing circuit of FIG. 3.

FIG. 6 is a diagram showing the flow of the DNN reconstruction processing implemented by the processing circuit 11. As illustrated in FIG. 6, the processing circuit 11 first enters k-space data containing a signal defect (step SA1). As the k-space data containing a signal defect, k-space data that contains a data defect may be entered. When the k-space trajectory scheme is Cartesian scanning, such k-space data may be acquired by MR imaging in which the number of phase encode steps is reduced. When the k-space trajectory scheme is radial scanning, the k-space data may be acquired by MR imaging in which the number of collection lines is reduced.

After step SA1, the processing circuit 11 implements the classification function 112 (step SA2). At step SA2, the processing circuit 11 determines the class value of the k-space data entered at step SA1. The processing circuit 11 may automatically determine the class value corresponding to the imaging conditions of the k-space data, or may determine the class value in accordance with the user's command entered by way of the input interface 15. In consideration of the imaging conditions that are wide-ranging, the imaging conditions targeted for classification may be determined in accordance with the user's command entered by way of the input interface 15.

For instance, if a learned model 131 that can be reassembled in accordance with the type of pulse sequence from among the imaging conditions is adopted, the class value may be determined in accordance with the type of pulse sequence of the entered k-space data.

After step SA2, the processing circuit 11 implements the activation control function 113 (step SA3). At step SA3, the processing circuit 11 adjusts the level of activation (layer-switching parameter) for a channel of the learned model 131 in accordance with the class value determined at step SA2. For this operation, the processing circuit 11 searches the table 133, using the class value determined at step SA2 as a search key, and identifies a layer-switching parameter associated with the class value for each channel. Then, the processing circuit 11 adjusts the layer-switching parameter of each channel of the learned model 131 to the identified layer-switching parameter. In addition, the processing circuit 11 counts the number of units that are turned off in each layer, determines the compensation parameter based on the total number of units and the number of units that are turned off, and sets the compensation parameter to the scaler.

After step SA3, the processing circuit 11 implements the reconstruction calculation function 114 (step SA4). At step SA4, the processing circuit 11 executes an FFT on the k-space data entered at step SA1 to generate reconstructed image data. Because of the signal defect contained in the k-space data entered at step SA1, the image quality of the reconstructed image data generated at step SA4 is degraded. The reconstructed image data generated at step SA4 will be referred to as provisional reconstruction image data. When a signal defect portion is contained in the k-space data, the processing circuit 11 may execute zero-padding to add the value 0 to the signal defect portion. The processing circuit 11 may execute the FFT on the zero-padded k-space data to generate the reconstructed image data.

After step SA4, the processing circuit 11 implements the forward propagation function 115 (step SA5). At step SA5, the processing circuit 11 applies the learned model 131 in which the layer-switching parameter has been adjusted at step SA3 to the provisional reconstruction image data generated at step SA4, and thereby generates the reconstructed image data with the signal defect portion restored. Because the level of activation for each unit of the learned model 131 has been adjusted in accordance with the class of the input medical signal, the reconstructed image data can be restored at high efficiency with high precision.

After step SA5, the processing circuit 11 implements the display control function 117 (step SA6). At step SA6, the processing circuit 11 displays the reconstructed image data generated at step SA5 on the display 19. In this manner, the user is enabled to observe a reconstructed image in which a signal defect portion is restored.

With the above operations, the DNN reconstruction processing is terminated.

The process flow of the above DNN reconstruction is explained merely as an example, and should not be limited to this. The order of steps SA1 to SA6 may be suitably altered.

For instance, the provisional reconstruction image data generating step (step SA4) may be placed between the k-space data entering step (step SA1) and the class value determining step (step SA2). Furthermore, at step SA6, where the reconstructed image data is displayed on the display 19, the reconstructed image data may instead be output to the memory 13 or a portable memory medium such as a universal serial bus (USB) memory, or output to a different device via the communication interface 17.

As described above, the medical signal processing apparatus 1 includes the processing circuit 11. The processing circuit 11 is provided at least with the activation control function 113 and the forward propagation function 115. With the activation control function 113, the processing circuit 11 adjusts the level of activation in accordance with the class of the imaging condition of the process target medical signal, for the units of the learned model 131. With the forward propagation function 115, the processing circuit 11 applies the learned model 131 in which the level of activation has been adjusted, to the medical signal, and generates an output signal.

With the above configuration, the medical signal processing apparatus 1 can realize the reassembly of the learned model 131 after model generation, in accordance with the class of the imaging condition of the process target medical signal. In this manner, the present invention offers the learned model 131 that produces machine learning output suitable for the imaging conditions of the process target medical signals, while maintaining the general versatility of the learned model 131.

Thus, the machine learning output can be achieved at high efficiency with high precision in accordance with the imaging conditions of the medical signals.

The user may not wish to change the layer-switching parameters in accordance with the class. To fit this need, the processing circuit 11 may display a graphical user interface (GUI) or the like on the display 19 before the DNN reconstruction so that the user can select whether or not to adjust the layer-switching parameters. If the adjustment of the layer-switching parameters is selected on the input interface 15 or the like, the processing circuit 11 implements the activation control function 113 as described above, and adjusts the layer-switching parameters in accordance with the class. If non-adjustment of the layer-switching parameters is selected, the processing circuit 11 implements the activation control function 113 to set all the layer-switching parameters to the ON value. Thereafter, the processing circuit 11 applies the learned model 131 to the entered medical image.

Next, the model learning apparatus 5 will be discussed.

Figure 7:
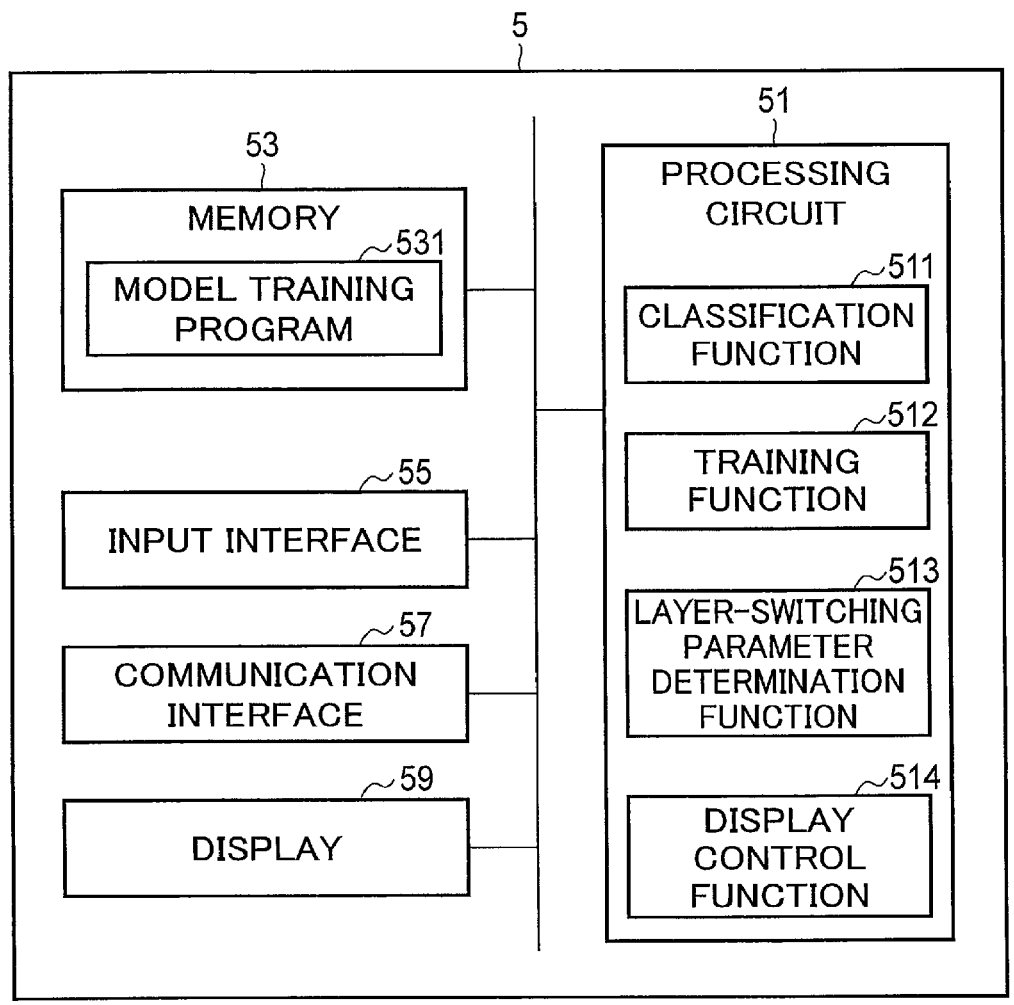
FIG. 7 is a diagram showing the configuration of the model learning apparatus in FIG. 1.

FIG. 7 is a diagram showing the configuration of the model learning apparatus 5. As illustrated in FIG. 7, the model learning apparatus 5 includes, as hardware resources, a processing circuit 51, a memory 53, an input interface 55, a communication interface 57 and a display 59.

The processing circuit 51 includes a processor such as a CPU and GPU. By activating a model training program 531 installed in the memory 53 or the like, the processor implements a classification function 511, training function 512, layer-switching parameter determination function 513, display control function 514, and the like. Each of the functions 511 to 514 does not always have to be realized by a single processing circuit. A plurality of independent processors may be combined into a processing circuit, and each of the processors may execute the program to realize the functions 511 to 514.

With the classification function 511, the processing circuit 51 classifies the process target medical signal in accordance with the imaging condition of the medical signal, and determines the class value. The classification function 511 of the processing circuit 51 is basically the same as the classification function 112 of the processing circuit 11 in the medical signal processing apparatus 1.

With the training function 512, the processing circuit 51 trains parameters of the multi-layered network based on the training data for a plurality of imaging conditions. The processing circuit 51 according to the present embodiment separately trains the parameters for the common unit and for the individual unit. Through the parameter training with the training function 512, the learned model 131 having a configuration illustrated in FIG. 4 is generated.

With the layer-switching parameter determination function 513, the processing circuit 51 determines the layer-switching parameter value for each of the units included in the multi-layered network. Furthermore, the processing circuit 51 generates the table 133 that describes layer-switching parameter values for each unit in accordance with different classes.

With the display control function 514, the processing circuit 51 displays the training data, training results, imaging conditions, classes, class values, layer-switching parameters, and the like on the display 59.

The memory 53 is a storage device such as a ROM, RAM, HDD, SSD, integrated circuit storage device or the like for storing various kinds of information. The memory 53 may store a model training program 531 for training the multi-layered network. Instead of the above storage device, the memory 53 may be a portable storage medium such as a CD, DVD, and a flash memory, or a drive device that reads and writes various types of information from and to a semiconductor memory element such as a RAM. The memory 53 may be provided in a computer coupled to the model learning apparatus 5 via a network.

The input interface 55 receives various input operations from the user, converts the received input operations into electric signals, and outputs the signals to the processing circuit 51. Specifically, the input interface 55 is coupled to input devices such as a mouse, a keyboard, a track ball, a switch, a button, a joystick, a touch pad and a touch panel display. The input interface 55 outputs to the processing circuit 51 an electric signal corresponding to the input operation to the input device. Furthermore, the input device coupled to the input interface 55 may be an input device provided in a computer coupled via a network or the like.

The communication interface 57 is an interface for performing data communications with the medical signal processing apparatus 1, the medical imaging apparatus 3, and the training data storage apparatus 7, as well as other computers.

The display 59 displays various types of information in accordance with the display control function 514 of the processing circuit 51. For instance, the display 59 displays the training data, training results, imaging conditions, classes, class values, layer-switching parameters, and the like. The display 59 further outputs a GUI or the like for receiving various operations from the user. As the display 19, a liquid crystal display, a CRT display, an organic electroluminescence display, a plasma display, or any other display may be suitably adopted.

Next, the example operations of the model learning apparatus 5 according to the present embodiment will be explained.

Figure 8:
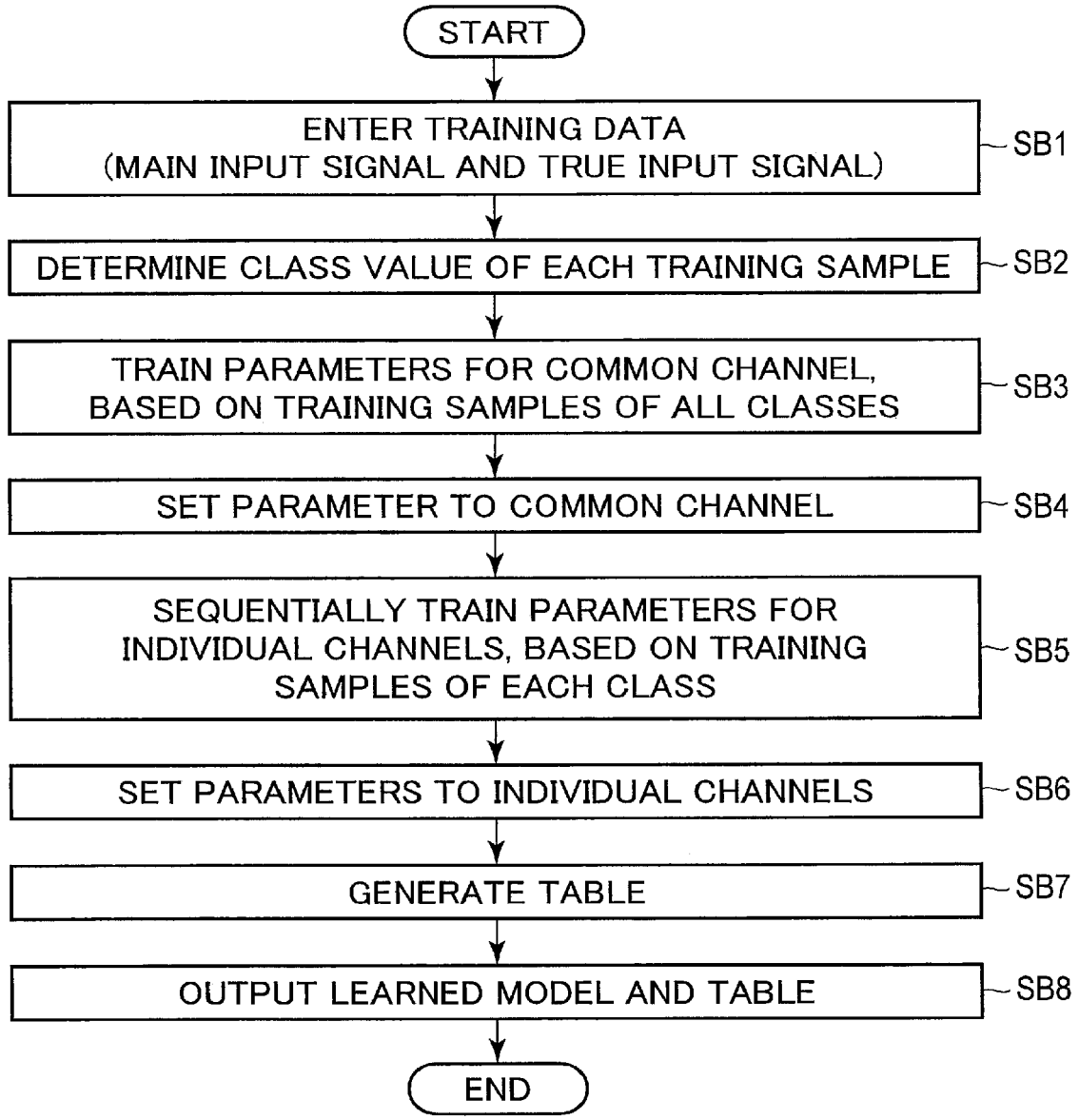
FIG. 8 is a diagram showing the flow of a learning process implemented by the processing circuit in FIG. 7.

FIG. 8 is a diagram showing a typical flow of the learning process implemented by the processing circuit 51. As illustrated in FIG. 8, the processing circuit 51 first enters the training data relating to a plurality of imaging conditions (classes) (step SB1). The training data includes a plurality of training samples relating to a plurality of classes. Each training sample includes a main input signal acquired under an imaging condition of a certain class and containing a signal defect portion, and a true input signal corresponding to the main input signal and containing no signal defect portion. As training samples, at least the samples of any class with which the to-be-generated learned model 131 can be reassembled are adopted. For instance, if the learned model 131 that can be reassembled in accordance with the EPI, FSE and FE illustrated in FIG. 5 is to be generated, at least the training samples that belong to the imaging conditions (classes) of the EPI, FSE and FE are adopted. It is preferable if a plurality of training samples are involved for each class.

After step SB1, the processing circuit 51 implements the classification function 511 (step SB2). At step SB2, the processing circuit 51 determines a class value in accordance with the imaging conditions (classes) of each training sample contained in the training data.

After step SB2, the processing circuit 51 implements the training function 512 (steps SB3 to SB6). With the training function 512, the processing circuit 51 generates or reads an untrained multi-layered network for which parameters are not yet trained. It is assumed here that a layer-switching parameter is preassigned to each unit of each layer in the untrained multi-layered network. Initially, the layer-switching parameter is set to the ON value.

At step SB3, the processing circuit 51 trains, based on the training samples of all the classes entered at step SB1, the parameter for the common channel of the multi-layered network. As the parameter training method, various known parameter training methods may be adopted. For example, the processing circuit 51 performs forward propagation on an input medical signal through the common channel of the multi-layered network, and calculates an estimated output signal corresponding to the input medical signal. Thereafter, the processing circuit 51 performs backpropagation on an error through the common channel of the multi-layered network, and calculates a gradient vector. The error is defined as a difference between the estimated output signal and true output signal. Then, the processing circuit 51 updates the parameter of the common channel in the multi-layered network, based on the gradient vector. Specifically, the processing circuit 51 updates the parameter so that the estimated output medical signal and the true output medical signal can approximate each other. A parameter that meets a certain converging condition or a parameter that is obtained after being updated for a predetermined number of times is determined as a final parameter for the common channel.

After step SB3, the processing circuit 51 sets the parameter finally determined at step SB3 as the parameter of the common channel (step SB4).

After step SB4, the processing circuit 51 sequentially trains the parameters for the individual channels of the multi-layered network, based on the training samples of each class that can be reassembled for the to-be-generated learned model (step SB5). For instance, when training samples for the EPI, FSE and FE in FIG. 5 are adopted, the parameters of the individual channels are trained using the training samples for EPI, then the parameters of the individual channels are trained using the training samples for FSE, and finally the parameters of the individual channels are trained using the training samples for FE.

As the parameter training method for individual channels, various known parameter training methods may be adopted. For example, the processing circuit 51 may perform forward propagation on the input medical signal through the individual channels of the multi-layered network, and calculate the estimated output signal corresponding to the input medical signal. Thereafter, the processing circuit 51 may perform backpropagation on the error through the individual channels of the multi-layered network, and calculate the gradient vector. The error is defined as a difference between the estimated output signal and true output signal. Next, the processing circuit 51 updates the parameters of the individual channels of the multi-layered network, based on the gradient vector. Specifically, the processing circuit 51 updates the parameters so that the estimated output medical signal and the true output medical signal can approximate each other. A parameter that meets a certain converging condition or a parameter obtained after being updated for a predetermined number of times is determined as a final parameter for the individual channel.

After step SB5, the processing circuit 51 sets the parameter finally determined at step SB5 to the parameter of the individual channel (step SB6). In this manner, the learned model 131 is completed.

After step SB6, the processing circuit 51 implements the layer-switching parameter determination function 513 (step SB7). At step SB7, the processing circuit 51 determines the layer-switching parameter value of each channel for each class, and thereby generates a table.

The details of steps SB3 to SB7 are now provided.

Figure 9:
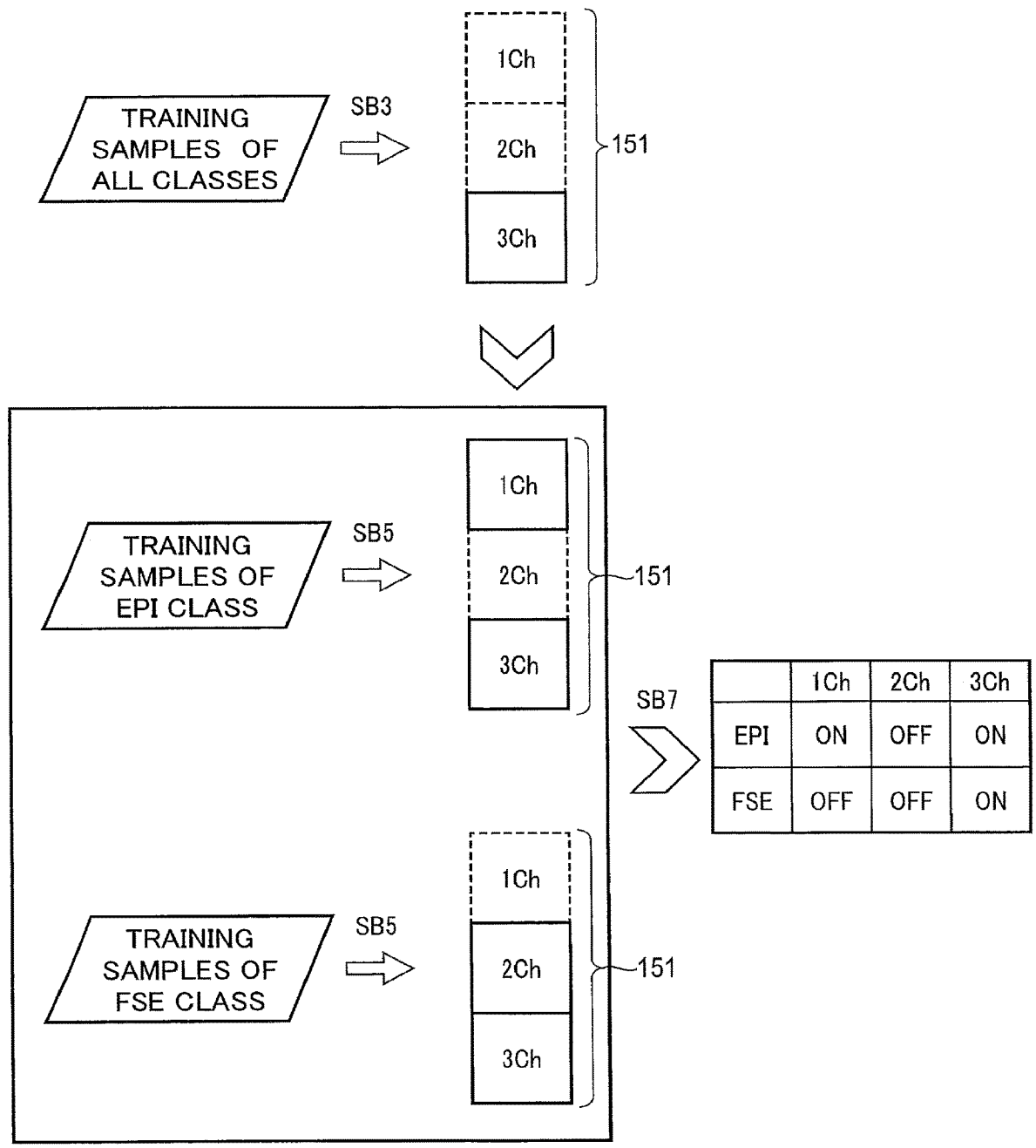
FIG. 9 is a diagram schematically showing the operations at steps SB3 to SB7 of FIG. 8 in the first learning method.

FIG. 9 is a diagram schematically showing the operations of steps SB3 to SB7 in FIG. 8. In FIG. 9, the classification-target imaging conditions are types of pulse sequences, which specifically include EPI and FSE. The units of the untrained multi-layered network 151 are classified into the first individual channel (1Ch), second individual channel (2Ch), and common channel (3Ch).

As illustrated in FIG. 9, the parameters of the common channel are trained at step SB3, based on the training samples of all the classes. The following two methods may be considered as the common channel setting method.

Addition-type setting: All the units included in each layer of the multi-layered network are determined as a common channel. The parameter training is performed by treating all the units as the units of the common channel. A layer-switching parameter is assigned to each unit of the common channel. At the time of training the parameters for the common channel, the layer-switching parameter is set to the ON value. Individual channels will be added after the parameter training of the common channel.

Switching-type setting: A plurality of units included in each layer of the multi-layered network are divided beforehand into a common channel and individual channel. A layer-switching parameter is assigned to each of the units of the common channel and individual channels. When training the parameter of the common channel, the layer-switching parameter of the common channel is set to the ON value, while the layer-switching parameter of the units of the individual channels is set to the OFF value.

When the parameter training of the common channel (3Ch) is completed, the parameters of the individual channels (1Ch and 2Ch) are trained for each class. For example, the parameter of the first individual channel (1Ch) is trained based on the training samples of the EPI class, and the parameter of the second individual channel (2Ch) is trained based on the training samples of the FSE class. In the following description, the parameter training for an individual channel will be explained separately for the case of the addition-type setting and for the case of the switching-type setting.

Addition-type setting: A unit is newly added to each layer of the multi-layered network 151. A layer-switching parameter is assigned to the added unit. The added unit is determined as the first individual channel (1Ch) for the EPI class. During the parameter training, the layer-switching parameter values of the first individual channel and the common channel are set to the ON value. The parameters are trained for the units that belong to the first individual channel, based on the training samples of the EPI class. The initial value of the parameter for the units that belong to the first individual channel may be set to any value, for example, to 0. During the parameter training for the first individual channel, the parameter for the common channel is fixed to the value that has been set at step SB4.

When the parameter training for the EPI channel is completed, a new unit is further added to each layer of the multi-layered network 151. A layer-switching parameter is assigned to the added unit. The added unit is determined as the second individual channel (2Ch) for the FSE class. During the parameter training, the layer-switching parameter values for the second individual channel and the common channel are set to the ON value, while the layer-switching parameter for the first individual channel is set to the OFF value. The parameters for the units that belong to the second individual channel are trained by using the training samples of the FSE class. The initial value of the parameter for the units that belong to the second individual channel may be set to any value, for example, to 0. During the parameter training for the second individual channel, the parameter for the common channel is fixed to the value that has been set at step SB4.

Switching-type setting: When the parameter training is performed in relation to the first individual channel (1Ch) for the EPI class, the layer-switching parameters for the first individual channel (1Ch) and the common channel (3Ch) are set to the ON value, while the layer-switching parameter for the second individual channel (2Ch) is set to the OFF value. With these settings, the parameter for the first individual channel is trained based on the training samples of the EPI class. The initial value of the parameter for the first individual channel may be set to any value, for example, to 0. During the parameter training for the first individual channel, the parameter for the common channel is fixed to the value that has been set at step SB4.

Next, the layer-switching parameters for the second individual channel (2Ch) for the FSE class and the common channel (3Ch) are set to the ON value, and the layer-switching parameter for the first individual channel (1Ch) is set to the OFF value. With these settings, the parameter for the second individual channel is trained based on the training samples of the FSE class. The initial value of the parameter for the units that belong to the second individual channel may be set to any value, for example, to 0. During the parameter training for the second individual channel, the parameter for the common channel is fixed to the value that has been set at step SB4.

The parameter training for the individual channel shown in FIG. 9 has been explained. The number of units in the common channel and an individual channel may be suitably determined. The number of units in the common channel may be the same as, or different from, the number of units in an individual channel. Among the individual channels, the number of units in one individual channel may be the same as, or different from another.

Once the parameters of the individual channels are trained, a table is generated at step SB7. For example, the processing circuit 51 generates the table based on the channels to which the units belong and the classes that correspond to the channels. For example, the layer-switching parameter value for the common channel is set ON (to ON value) for any of the classes. With regard to the layer-switching parameter values for the individual channels, the layer-switching parameter value for the class corresponding to an individual channel is set ON, and the layer-switching parameter value for the class that does not correspond to this individual channel is set OFF (to OFF value). In particular, as illustrated in FIG. 9, with regard to the EPI class, the layer-switching parameter value for the common channel (3Ch) is set ON, the layer-switching parameter value for the EPI channel (1Ch) is set ON, and the layer-switching parameter value for the FSE channel (2Ch) is set OFF. With regard to the FSE class, the layer-switching parameter value for the common channel (3Ch) is set ON, the layer-switching parameter value for the EPI channel (1Ch) is set OFF, and the layer-switching parameter value for the FSE channel (2Ch) is set ON.

In the above explanation of FIG. 9, the individual channel that is not a training target during the parameter training for an individual channel is deemed as either not existing or being non-activated. However, the parameter training method for the individual channels according to the present embodiment is not limited to the above.

Figure 10:
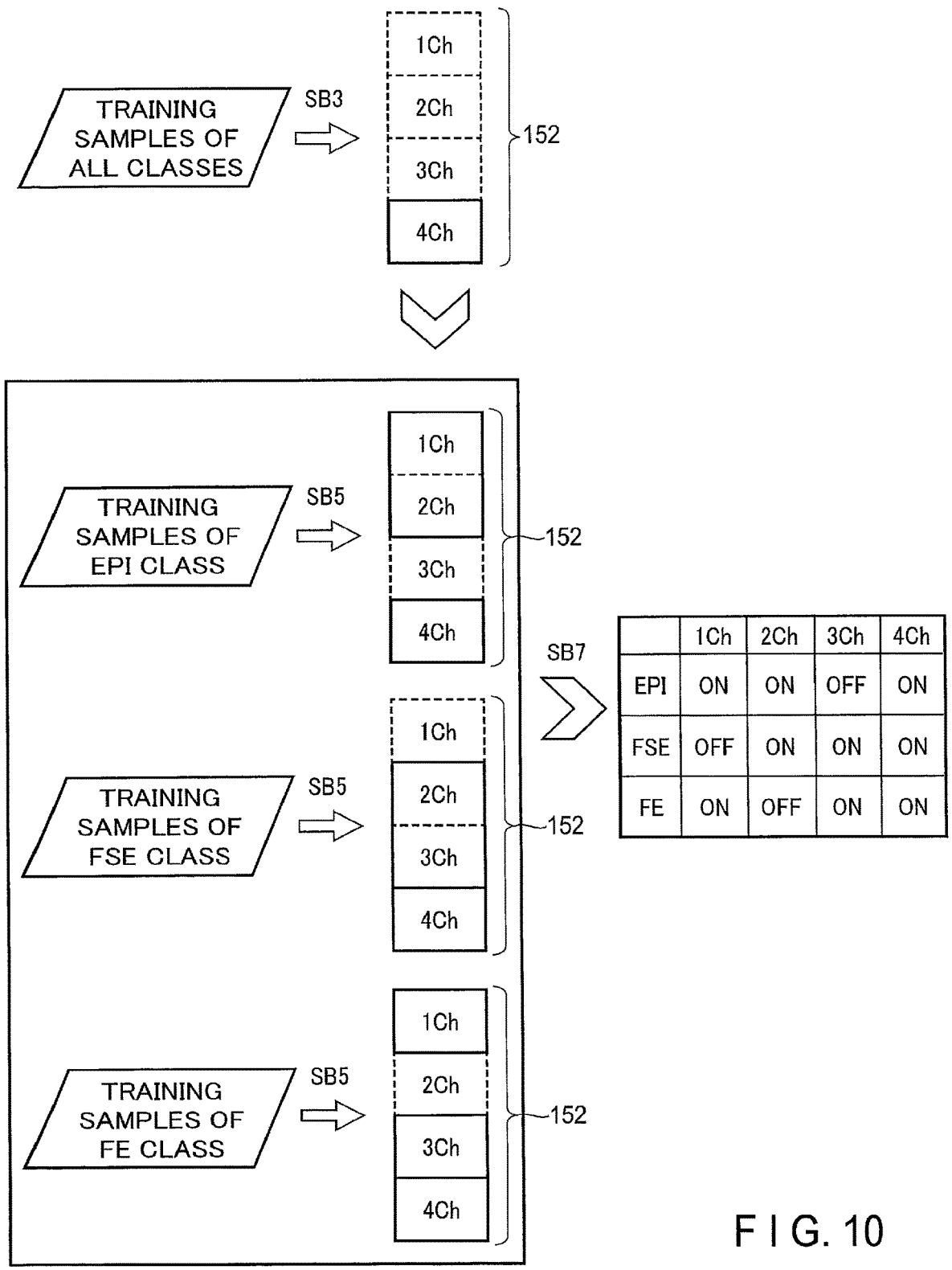
FIG. 10 is a diagram schematically showing the operations at steps SB3 to SB7 of FIG. 8 in the second learning method.

FIG. 10 is a diagram schematically showing the operations of steps SB3 to SB7 in FIG. 8. In FIG. 10, the classification-target imaging conditions are types of pulse sequences, which specifically include EPI, FSE and FE. The units of the untrained multi-layered network 152 are classified into the first individual channel (1Ch), second individual channel (2Ch), third individual channel (3Ch) and common channel (4Ch).

For the training method of FIG. 10, the addition type and the switching type are both applicable as the common channel setting method. The parameter training method for the common channel is the same as FIG. 9, and therefore the explanation is omitted.

The training method for the individual channels is the same, regardless of the type of the setting method for the common channel. As illustrated in FIG. 10, the processing circuit 51 trains the parameters based on the training samples of each class, using all the individual channels (set of 1Ch, 2Ch and 3Ch) for each class. Here, the processing circuit 51 monitors the outputs of the units that belong to the individual channels, and calculates the contribution level of each unit to the estimated output signal of the multi-layered network. A unit having a contribution level higher than a threshold value is set to the channel of the class. The threshold value may be determined as needed. During the parameter training, the layer-switching parameters for the individual channel and common channel are all set to the ON value.

As illustrated in FIG. 10, the parameters of the individual channels (set of 1Ch, 2Ch and 3Ch) are trained using the training samples of the EPI class. Here, the output of each unit is monitored to calculate the level of contribution of each unit to the estimated output signal. The set of units having a contribution level higher than a threshold value is classified as a channel for the EPI class. The process is executed similarly with regard to the FSE class and FE class. In this manner, the parameter training for the individual channels and classification of classes of units can be realized. In FIG. 10, the channel related to the EPI class is determined as the set of the first and second channels, the channel related to the FSE class is determined as the set of the second and third channels, and the channel related to the FE class is determined as the set of the first and third channels.

As described above, with the training method of FIG. 10, one individual channel can be associated with a plurality of classes. Thus, the number of units can be reduced in comparison to the training method of FIG. 9. On the other hand, with the training method of FIG. 9, a single individual channel is associated with a single class, and therefore the optimization for the class can be realized.

When the parameter training for the individual channels is completed, the table is generated at step SB7. For example, the processing circuit 51 generates the table based on the channels to which units belong and the classes that correspond to the channels. For instance, the layer-switching parameter value of the common channel (4Ch) is set ON for all the classes. As for the layer-switching parameter values of the individual channels, the value is ON for the class that is associated with an individual channel, and OFF for the class that is not associated. In particular, as illustrated in FIG. 10, with regard to the EPI class, the layer-switching parameter value for the common channel (4Ch) is set ON, the layer-switching parameter value for the EPI channel (set of 1Ch and 2Ch) is set ON, and the layer-switching parameter value for the third individual channel (3Ch) is set OFF. With regard to the FSE class, the layer-switching parameter value for the common channel (4Ch) is set ON, the layer-switching parameter value for the FSE channel (set of 2Ch and 3Ch) is set ON, and the layer-switching parameter value for the first individual channel (1Ch) is set OFF. With regard to the FE class, the layer-switching parameter value for the common channel (4Ch) is set ON, the layer-switching parameter value for the FE channel (set of 1Ch and 3Ch) is set ON, and the layer-switching parameter value for the second individual channel (2Ch) is set OFF.

After step SB7, the processing circuit 51 outputs the learned model 131 and the table 133 (step SB8). For example, the processing circuit 51 may send the learned model 131 and the table 133 to the medical signal processing apparatus 1 via the communication interface 57, or store it in the memory 53.

With the above operations, the DNN reconstruction processing is terminated.

As described above, the model learning apparatus 5 includes the processing circuit 51. This processing circuit 51 realizes at least the training function 512 by implementing the model training program 531. With the training function 512, the processing circuit 51 generates a learned model 131 having layer-switching parameters attached to the units, based on a plurality of medical signals relating to a plurality of imaging conditions, where each of the layer-switching parameters is a variable for adjusting the level of activation of a unit in accordance with the imaging condition. Furthermore, with the training function 512, the processing circuit 51 trains, based on a plurality of medical signals relating to a plurality of imaging conditions, the parameter of the first units associated with all the imaging conditions, from among all the units. Then, the processing circuit 51 trains, based on the medical signals relating to an imaging condition of the plurality of imaging conditions, the parameter of the second unit that is different from the first unit and associated with this imaging condition, from among the plurality of units.

With the above configuration, the model learning apparatus 5 can generate a learned model 131 that can be reassembled in accordance with the classes of the imaging conditions for a process target medical signal.

Next, a specific example of the DNN reconstruction processing will be described. The learned model for the DNN reconstruction processing is a deep neural network (DNN), which is a multi-layered network model designed to resemble the neural circuit of the brain of a living being. In particular, the learned model includes, as a DNN, a convolutional neural network (CNN) that restores a signal defect.

Figure 11:
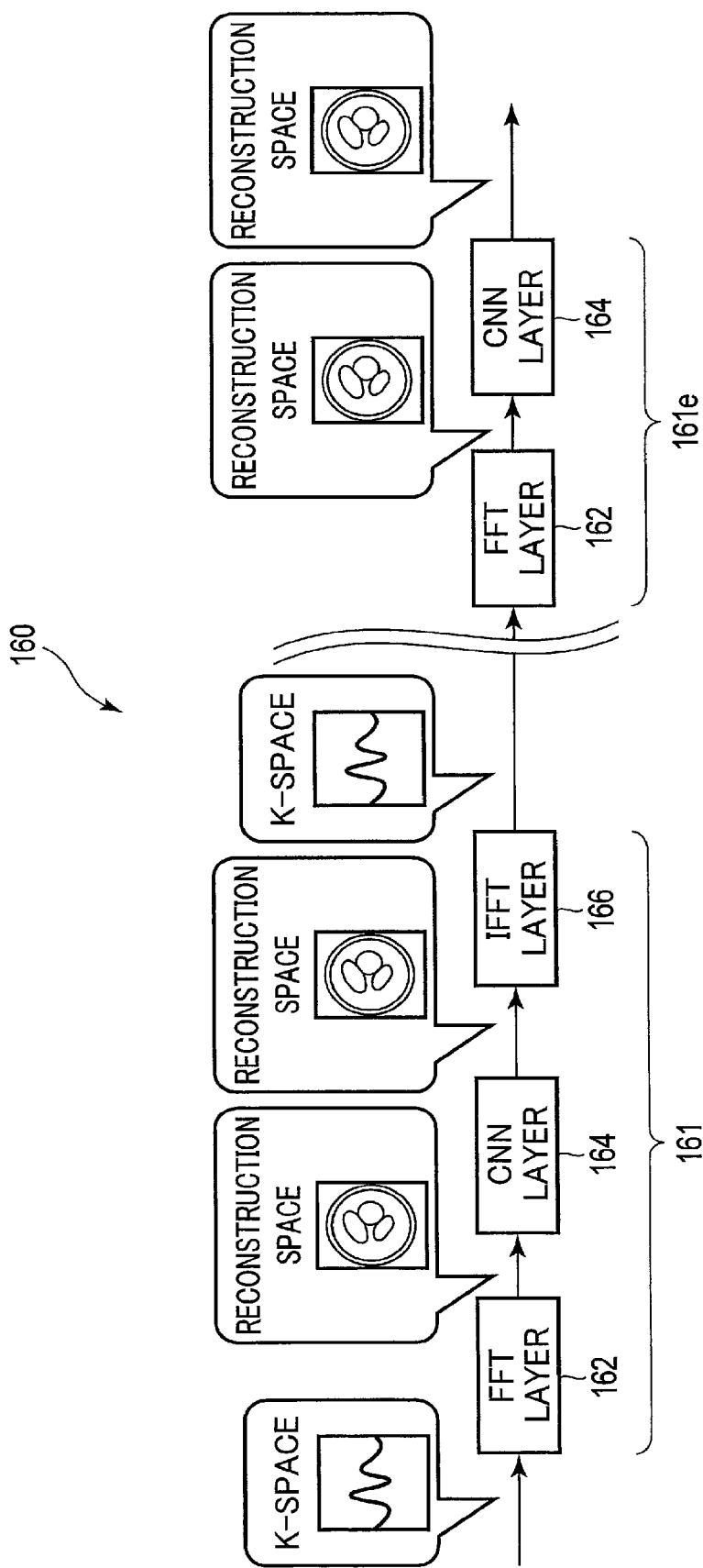
FIG. 11 is a diagram showing an example configuration of a learned model that is adopted for DNN reconstruction processing according to the present embodiment.

FIG. 11 is a diagram showing an example configuration of a learned model 160 that is used for the DNN reconstruction processing. As illustrated in FIG. 11, the learned model 160 has a chain structure in which unit network structures 161 each including a fast Fourier transfer (FFT) layer 162, a CNN layer 164 and an inverse fast Fourier transfer (IFFT) layer 166 are connected to each other to form a cascade connection. The k-space data is entered to the FFT layer 162, where the FFT is applied to the entered k-space data, thereby the reconstructed image data is output. The CNN layer 164 is the learned model 131 generated by the model learning apparatus 5. That is, the CNN layer 164 is configured to be reassembled in accordance with the class of the input reconstruction image data containing a signal defect. This input reconstruction image data is entered to the CNN layer 164, and reconstructed image data having a signal defect portion restored is output. The reconstructed image data is entered to the IFFT layer 166, where the IFFT is applied to the input reconstruction image data, and thereby the k-space data is output. The output data from the unit network structure 161 has the same number of dimensions and the same resolution as the input data.

The chain structure, in which the output of the unit network structure 161 becomes the input of the next unit network structure 161, improves the restoration accuracy of the signal defect portion. The CNN layer 164 is implemented by the forward propagation function 115 of the processing circuit 11. The FFT layer 162 and the IFFT layer 166 may be implemented as part of the forward propagation function 115 of the processing circuit 11, or as the reconstruction calculation function 114.

As illustrated in FIG. 11, if the reconstructed image data is to be output as an output of the learned model 160, the last unit network structure 161e of the learned model 160 should be provided with an FFT layer 162 and CNN layer 164 but not an IFFT layer 166. If the k-space data is to be output as an output of the learned model 160, the last unit network structure 161e should be provided with an FFT layer 162, a CNN layer 164 and an IFFT layer 166, in the same manner as other unit network structures 161. The learned model 160 may be stored in the memory 13 of the medical signal processing apparatus 1.

The structure of the learned model 160 may be suitably designed in accordance with the intended purpose. For example, a matching layer may be provided downstream of the IFFT layer 166. The processed k-space data that is output from the CNN layer 164 based on the provisional reconstruction image data, and the k-space data that is entered to the learned model 160 and is not yet processed, are entered to the matching layer so that a matching process can be implemented on the processed k-space data using the unprocessed k-space data, as a result of which matching-processed k-space data is output. The k-space data subjected to the matching process is weighted for each pixel by the unprocessed k-space data in accordance with the degree of the signal defect. For example, a greater weight is assigned to the pixel value of the unprocessed k-space data as the degree of the signal defect lowers, whereas a smaller weight is assigned to the pixel value of the unprocessed k-space data as the degree of the signal defect rises. In this manner, the matching of the processed k-space data and the unprocessed k-space data can be ensured.

The learned model 160 is applicable to medical signals acquired by a medical image diagnostic apparatus other than a magnetic resonance imaging apparatus. For example, when the learned model 160 is applied to the raw data acquired by an X-ray computed tomography imaging apparatus, the FFT layer 162 may be replaced with an inverse Radon transform layer, and the IFFT layer 166 may be replaced with a Radon transform layer. In the inverse Radon transform layer, an inverse Radon transform such as FBP is carried out on the raw data so that CT image data can be reconstructed. In the Radon transform layer, a Radon transform is carried out on the CT image data so that raw data can be attained.

Examples of the raw data of the X-ray computed tomography imaging apparatus may include integral data indicating the integral of radiation dose, and spectral CT data indicating the number of counts in accordance with X-ray energy levels. The class of the integral data may be integral scanning, and the class of the spectral CT data may be spectral CT scanning. As the integral scanning, dual energy scanning may be performed to realize CT scanning by switching the high voltage between two values.

Next, a specific example of the activation control will be described.

Example 1

FIG. 12 is a diagram schematically showing an example of the activation control. It is assumed in FIG. 12 that the classification-target imaging condition is a phase encoding direction. The reconstructed image data acquired by the EPI contains noise streaks corresponding to the phase encoding direction. In particular, noise streaks that run in a direction orthogonal to the phase encoding direction appear on a reconstructed image. For example, when the phase encoding direction is the vertical direction with respect to a reconstructed image, horizontal noise streaks appear on the reconstructed image. When the phase encoding direction is the horizontal direction with respect to the reconstructed image, vertical noise streaks appear on the reconstructed image.

When the classification-target imaging condition is the phase encoding direction, the units of the learned model are classified into a common channel that are used commonly for reduction of vertical noise streaks and horizontal noise streaks, the first individual channel used for reduction of vertical noise streaks, and the second individual channel used for reduction of horizontal noise streaks. For instance, a learned model may be designed with the common channel including the first to 32nd units, the first individual channel including the 33rd to 48th units, and the second individual channel including the 49th to 64th units. The learned model is generated in accordance with the learning process of FIG. 8, based on medical images having the vertical phase encoding direction and medical images having the horizontal phase encoding direction.

As illustrated at the top of FIG. 12, when the class of the input medical image is the phase encoding direction that is a vertical direction, the layer-switching parameters of the common channel and second individual channels are set to the ON value, while the layer-switching parameter of the first individual channel is set to the OFF value. In this manner, the horizontal noise streaks of the input medical image can be effectively reduced. When the class of the input medical image is the phase encoding direction that is a horizontal direction, as illustrated at the bottom of FIG. 12, the layer-switching parameters of the common channel and the first individual channel are set to the ON value, while the layer-switching parameter of the second individual channel is set to the OFF value. In this manner, the noise reduction from the input medical image can be effectively achieved at high accuracy.

Example 2

The imaging-target body parts may serve as classification-target imaging conditions. The body parts may be a head, abdomen, neck, limbs, or heart. If this is the case, the learned model is generated in accordance with the learning process of FIG. 8, based on the medical images of two imaging-target body parts or more. In particular, when a learned model is generated to be reassembled in accordance with the head, abdomen, and heart, a learned model is generated based at least on a cranial medical image, abdominal medical image and cardiac medical image. For this case, the learned model includes the first individual channel for reducing head-specific noise, the second individual channel for reducing abdomen-specific noise, the third individual channel for reducing heart-specific noise, and the common channel for reducing noise common to the imaging body parts including the head, abdomen, and heart. When a cardiac medical image is applied to the learned model, the layer-switching parameters of the third individual channel and the common channel are set to the ON value, while the layer-switching parameters of the first individual channel and the second individual channel are set to the OFF value. In this manner, the noise reduction from the input medical image can be effectively achieved at high accuracy.

Example 3

The classification-target imaging conditions may be a data defect portion or data collection portion of the k-space data. For example, the k-space trajectory scheme in which the k-space data is acquired in a radial fashion along collection lines (spokes) having angles of 0 to 360 degrees will be considered. Whether to collect k-space data is determined with respect to each of the collection lines between 0 and 1 degree, 1 and 2 degrees, . . . 359 and 360 degrees, as a data defect portion or data collection portion. The learned model is generated based on the medical images having different data defect portions or different data collection portions, in accordance with the learning process of FIG. 8. An individual channel is formed for every combination of the data collection lines (data collection portions). For example, an individual channel is formed for reducing noise specific to an MR image, in which the collection lines between 0 and 1 degrees, 120 and 121 degrees and 240 and 241 degrees are data collection portions, and the lines at any other angles are data defect portions. In this case, the layer-switching parameters of the individual channels and common channel are set to the ON value, while the layer-switching parameters of other individual channels are set to the OFF value. In this manner, noise related to data defects can be effectively reduced at high accuracy from the input medical image.

A data defect portion or data collection portion may be set in accordance with a k-space collection mask pattern. For instance, the k-space may be divided into 16×16 blocks, and whether to collect k-space data is determined for each block as a data defect portion or data collection portion. The learned model is generated based on the medical images having different data defect portions or different data collection portions, in accordance with the learning process of FIG. 8. Here, individual channels for reducing block-specific noise and a common channel for reducing noise common to all the blocks are formed. If this is the case, the layer-switching parameters of the individual channel for reducing specific noise and the common channel are set to the ON value, and the layer-switching parameters of other individual channels are set to the OFF value. In this manner, noise related to data defects can be effectively reduced at high accuracy from the input medical image.

Application Example 1

According to the above examples, only the individual channel that corresponds to the class of the input medical signal is activated. The present embodiment, however, is not limited thereto. That is, the individual channel that corresponds to the class of an input medical signal only may be inactivated.

Figure 13:
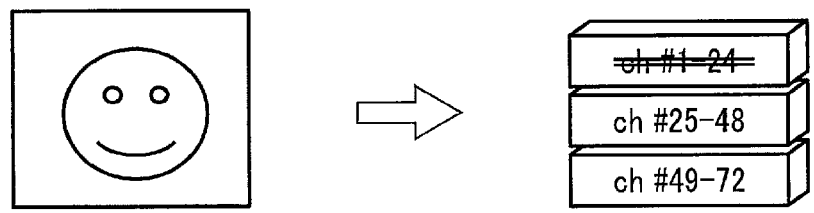
FIG. 13 is a diagram schematically showing an example activation control according to Application Example 1.
Figure 13:
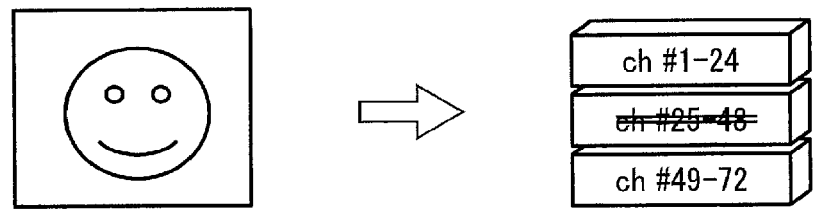
Figure 13:
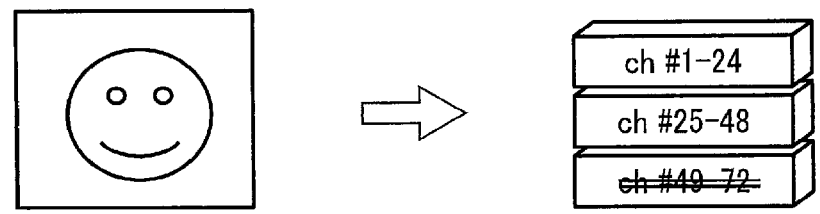

FIG. 13 is a diagram schematically showing an example activation control according to Application Example 1. As illustrated in FIG. 13, the classification-target imaging conditions are combinations of the type of pulse sequence and the type of k-space trajectory scheme. The reconstructed image data may contain various noises depending on the combination of a pulse sequence type and a k-space trajectory scheme type. The classes in FIG. 13 are pulse sequence=non-EPI, and k-space trajectory scheme=Cartesian; pulse sequence=non-EPI, and k-space trajectory scheme=radial; pulse sequence=EPI, and k-space trajectory scheme=unspecified.

With the above three classification-target imaging conditions, the units of the learned model may be classified into the first individual channel, which is not activated if pulse sequence=non-EPI and k-space trajectory scheme=Cartesian; the second individual channel, which is not activated if pulse sequence=non-EPI and k-space trajectory scheme=radial; and the third individual channel, which is not activated if pulse sequence=EPI and k-space trajectory scheme-unspecified. If the individual channel corresponding to the class of the input medical image only is inactivated, a common channel may not be arranged.

As illustrated in FIG. 13, the learned model may be designed in such a manner that the first individual channel includes the first to 24th units, the second individual channel includes the 25th to 48th units, and the third individual channel includes the 49th to 72nd units. The learned model is generated in accordance with the learning process of FIG. 8, based on medical images of the pulse sequence=non-EPI, and k-space trajectory scheme=Cartesian; medical images of the pulse sequence=non-EPI, and k-space trajectory scheme=radial; and medical images of the pulse sequence=EPI, and k-space trajectory scheme=unspecified. The first individual channel is a set of units that are inactivated only for a medical image of the pulse sequence=non-EPI, and k-space trajectory scheme=Cartesian. The second individual channel is a set of units that are inactivated only for a medical image of the pulse sequence=non-EPI, and k-space trajectory scheme=radial. The third individual channel is a set of units that are inactivated for a medical image of the pulse sequence=EPI, and k-space trajectory scheme=unspecified.

As illustrated at the top of FIG. 13, when the class of the input medical image is the pulse sequence=non-EPI and k-space trajectory scheme=Cartesian, the layer-switching parameters of the second and third individual channels are set to the ON value, while the layer-switching parameter of the first individual channel is set to the OFF value. As illustrated in the middle of FIG. 13, when the class of the input medical image is the pulse sequence=non-EPI and k-space trajectory scheme-radial, the layer-switching parameters of the first and third individual channels are set to the ON value, while the layer-switching parameter of the second individual channel is set to the OFF value. As illustrated at the bottom of FIG. 13, when the class of the input medical image is the pulse sequence-EPI and k-space trajectory scheme=unspecified, the layer-switching parameters of the first and second individual channels are set to the ON value, and the layer-switching parameter of the third individual channel is set to the OFF value. In this manner, noise can be effectively reduced in accordance with the combination of the pulse sequence and k-space trajectory scheme of the input medical image.

Application Example 2

According to the above examples, an individual channel is activated only for the class of an input medical signal.

Furthermore, according to Application Example 1, the individual channel is inactivated only for the class of an input medical signal. The present embodiment, however, is not limited thereto. That is, an individual channel that is activated only for the class of an input medical signal and an individual channel that is inactivated only for the class of an input medical signal may both be employed.

FIG. 14 is a diagram schematically showing an example activation control according to Application Example 2. In FIG. 14, the classification-target imaging condition is whether or not a noise specific to a certain type of pulse sequence is contained. The reconstructed image data may contain various kinds of noise depending on a pulse sequence. For example, when the pulse sequence is EPI, noise specific to the EPI appears on a reconstructed image. Hereinafter, noise specific to the EPI will be referred to as EPI noise. The classes in FIG. 14 are denoted in binary form including "1" indicating that EPI noise is contained and "0" indicating that EPI noise is not contained.

The units of the learned model in FIG. 14 are classified into a common channel that is activated when EPI noise=0 and 1 (i.e., both), the first individual channel that is inactivated only when EPI noise=1, and the second individual channel is activated only when EPI noise=1.

For example, as illustrated in FIG. 14, a learned model may be designed with the common channel including the first to 32nd units, the first individual channel including the 33rd to 48th units, and the second individual channel including the 49th to 64th units. The learned model is generated in accordance with the learning process of FIG. 8, based on medical images of EPI noise=1 and medical images of EPI noise=0. As a medical image of EPI noise=0, a medical image acquired by any pulse sequence other than EPI may be adopted.

If the class of an input medical image is EPI noise=1 as illustrated at the top of FIG. 14, the layer-switching parameters of the common channel and second individual channel are set to the ON value, while the layer-switching parameter of the first individual channel is set to the OFF value. If the class of an input medical image is EPI noise=0 as illustrated at the bottom of FIG. 14, the layer-switching parameters of the common channel and first individual channel are set to the ON value, while the layer-switching parameter of the second individual channel is set to the OFF value. In this manner, the noise reduction from the input medical image can be effectively achieved at high accuracy, depending on the presence/absence of EPI noise.

Application Example 3

In the above examples, the layer-switching parameter is in binary form including the ON value and OFF value. The present embodiment, however, is not limited thereto. The layer-switching parameter according to Application Example 3 may take three values or more: "1" indicating the ON value, "0" indicating the OFF value, and at least one intermediate value between "1" and "0". The value "1" denotes a higher level of activation than "0".

FIG. 15 shows an example table according to Application Example 3. As illustrated in FIG. 15, a class may be a type of pulse sequence. In particular, the types of pulse sequences may include EPI, gradient and spin echo (GRASE), and FSE. With a GRASE pulse sequence, a plurality of refocus pulses are applied by FSE, and the gradient field is switched by EPI to generate echoes between the refocus pulses being applied, thereby collecting the data. That is, the GRASE includes the properties of both EPI and FSE.

As illustrated in FIG. 15, the units are classified into the first channel, the second channel and the third channel.

The first channel and second channel are individual channels for which the layer-switching parameter of at least one of the classes is set to "0". In particular, the first channel is a classification of units that are activated specifically for the class "EPI", and the second channel is a classification of units that are activated specifically for the class "FSE". The third channel is a common channel that is activated for both classes.

When the class is "EPI", the layer-switching parameter is set to "1" for the first channel, "0" for the second channel, and "1" for the third channel. When the class is "FSE", the layer-switching parameter is set to "0" for the first channel, "1" for the second channel, and "1" for the third channel. When the class is "GRASE", the layer-switching parameter for each of the first channel and second channel is set to a value between "1" and "0" in accordance with the ratio of the EPI property and FSE property in GRASE. For instance, if the ratio of EPI property and FSE property in GRASE is fifty-fifty, the layer-switching parameter is set to "0.5" for the first channel, "0.5" for the second channel, and "1" for the third channel. If the ratio of EPI property and FSE property in GRASE is 7 to 3, the layer-switching parameter is set to "0.7" for the first channel, "0.3" for the second channel, and "1" for the third channel.

With the activation control function 113 according to Application Example 3, the processing circuit 11 multiplies the output of the units that belong to each channel by the layer-switching parameter of the corresponding channel. For instance, when the class is "EPI", the outputs of the units that belong to the first channel are multiplied by "1", the outputs of the units that belong to the second channel are multiplied by "0", and the outputs of the units that belong to the third channel are multiplied by "1". When the class is "GRASE", the outputs of the units that belong to the first channel are multiplied by "0.5" in the example of FIG. 15, the outputs of the units that belong to the second channel are multiplied by "0.5", and the outputs of the units that belong to the third channel are multiplied by "1".

The scaler according to Application Example 3 compensates for the reduced amount of the output values of the units having a layer-switching parameter value smaller than "1". For example, it is assumed that the number of units is 64. If 32 of these units have the layer-switching parameter that is set to "0.5", and the remaining units have the layer-switching parameter that is set to "1", the scaler multiplies the output value of the previous units by 64/(32×1+32×0.5)=64/48.

The learned model according to Application Example 3 may be generated in accordance with the learning process of FIG. 8, based on the training samples of the class to which the layer-switching parameter "1" or "0" is set. The training samples of the classes having the layer-switching parameter value other than "1" and "0" can be processed even if they are not used for parameter training. For example, the learned model corresponding to the table in FIG. 15 is generated based on the training samples of the EPI class and the training samples of the FSE class. After generating the learned model, the layer-switching parameters in the class of "GRASE" may be determined for each channel, based on the ratio of EPI properties and FSE properties in GRASE.

As described above, according to Application Example 3, with regard to the layer-switching parameters of a secondary class having intermediate properties between the original classes that are considered in the parameter learning, a learned model optimal for the secondary class can be reassembled by determining the layer-switching parameters based on the layer-switching parameter values of the related original classes. The above explanation of the embodiment is not limited to a method of learning without using training samples of classes of the layer-switching parameters other than "1" and "0". In addition to "1" and "0", the training data and intermediary layer-switching parameter in GRASE are provided, by use of which the parameter learning may be carried out.

The word "processor" used in the above explanation may be, for example, a CPU, a GPU, an application specific integrated circuit (ASIC), a programmable logic device (e.g., Simple Programmable Logic Device (SPLD), Complex Programmable Logic Device (CPLD), and field programmable gate array (FPGA)) or the like. The processor realizes the functions by reading and implementing the program stored in the storage circuit. Instead of storing the program in the memory circuit, the program may be directly incorporated in the circuit of the processor. If this is the case, the processor realizes the functions by reading and executing the program incorporated in the circuit. Instead of executing the program, the function corresponding to the program may be realized by a combination of logic circuits. Each processor of the present embodiment is not limited to a single circuit configured for each processor, but a plurality of independent circuits may be combined into a single processor that can realize the function. Moreover, the structural elements in FIGS. 1, 3 and 7 may be integrated into one processor to implement their functions.

With at least one of the above explained embodiments, the machine learning output can be achieved at high efficiency with high precision in accordance with the imaging conditions of the medical signals.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A medical signal processing apparatus comprising:
a processing circuit configured to:
read a learned model including a plurality of layers each including a plurality of channels, wherein each of the channels includes a plurality of units with a weight and a switching parameter assigned to each of the units, the weight is a parameter that is a target of training for the learned model, the switching parameter has a value for adjusting a level of activation of a corresponding one of the units, the value is common among units of the channel to which the corresponding unit belongs, and the switching parameter is not a target of training for the learned model;
obtain a process target medical signal;
adjust the level of activation of each of the plurality of units included in the learned model by setting the switching parameter to a value that corresponds to classification of an imaging condition for the process target medical signal; and
generate an output signal by applying the learned model in which the level of activation has been adjusted to the process target medical signal.

2. The medical signal processing apparatus according to claim 1, wherein
the level of activation is represented by binary values that indicate an ON state and OFF state of the unit.

3. The medical signal processing apparatus according to claim 1, wherein
the level of activation is represented by ternary values or more that include a value indicating an ON state of the unit, a value indicating an OFF state of the unit, and a value between the value indicating the ON state and the value indicating the OFF state.

4. The medical signal processing apparatus according to claim 1, wherein
the medical signal is data acquired by a magnetic resonance imaging apparatus, and
the imaging condition includes at least one of a pulse sequence type, a k-space trajectory scheme type, a phase encoding direction, an imaging body part and a k-space data defect portion with regard to the magnetic resonance imaging apparatus.

5. The medical signal processing apparatus according to claim 1, further comprising:
a memory to store a table in which the unit is associated with the level of activation with regard to each of a plurality of classes of imaging conditions,
wherein the processing circuit adjusts, using the table, the level of activation of the unit in accordance with a class of the imaging condition for the medical signal.

6. The medical signal processing apparatus according to claim 1, wherein
the unit includes a first unit that relates to all imaging conditions for all medical signals that are entered as training samples at a time of training the learned model, and a plurality of second units, each of which relates particularly to a single imaging condition or a plurality of imaging conditions of all the imaging conditions, and
the processing circuit increases the level of activation of the first unit and the level of activation of a unit of the second units that corresponds to a class, in comparison to the level of activation of a unit of the second units that does not correspond to the class.

7. The medical signal processing apparatus according to claim 1, wherein
the output signal has the same number of dimensions and same resolution as the medical signal.

8. The medical signal processing apparatus according to claim 1, wherein
the output signal represents a result of recognizing the medical signal.

9. The medical signal processing apparatus according to claim 1, wherein
the medical signal represents medical image data.

10. The medical signal processing apparatus as claimed in claim 1, wherein the processing circuitry configured to adjust the level of activation of each of the plurality of units comprises processing circuitry configured to (a) adjust the level of activation of a first group of units of the plurality of units included in the learned model in accordance with the classification of the imaging condition for the process target medical signal and (b) not adjust the level of activation of a second group of units of the plurality of units included in the learned model in accordance with the classification of the imaging condition for the process target medical signal, wherein the first and second groups are different.

11. The medical signal processing apparatus as claimed in claim 1, wherein the plurality of channels includes at least a first channel and a second channel, wherein the plurality of layers includes at least first and second layers, wherein the switching parameter of the first channel is applied to all units of the first channel in the first and second layers, wherein the switching parameter of the second channel is applied to all units of the second channel in the first and second layers, and wherein the switching parameter of the first channel is separately switched from the switching parameter of the second channel.

* * * * *